United States Patent
Sackner et al.

(10) Patent No.: US 6,551,252 B2
(45) Date of Patent: *Apr. 22, 2003

(54) SYSTEMS AND METHODS FOR AMBULATORY MONITORING OF PHYSIOLOGICAL SIGNS

(75) Inventors: Marvin A. Sackner, Miami Beach, FL (US); Dana Michael Inman, Miami, FL (US)

(73) Assignee: VivoMetrics, Inc., Ventura, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/836,384

(22) Filed: Apr. 17, 2001

(65) Prior Publication Data

US 2002/0032386 A1 Mar. 14, 2002

Related U.S. Application Data

(60) Provisional application No. 60/197,589, filed on Apr. 17, 2000.

(51) Int. Cl.[7] .............................. A61B 5/08; A61B 5/02; A61B 5/04
(52) U.S. Cl. ...................... 600/536; 600/388; 600/389; 600/301; 600/508; 600/509; 600/481
(58) Field of Search ................................ 600/536, 547, 600/529, 534, 509, 508, 483, 481, 390, 389, 388, 386, 301, 300, 587, 595

(56) References Cited

U.S. PATENT DOCUMENTS

| | | | | |
|---|---|---|---|---|
| 4,016,868 A | * | 4/1977 | Allison | 600/388 |
| 4,308,872 A | * | 1/1982 | Watson et al. | 600/534 |
| 4,373,534 A | * | 2/1983 | Watson | 600/534 |
| 4,572,197 A | * | 2/1986 | Moore et al. | 374/121 |
| 4,817,625 A | * | 4/1989 | Miles | 33/561.2 |
| 5,178,151 A | * | 1/1993 | Sackner | 600/485 |
| 5,331,968 A | * | 7/1994 | Williams et al. | 600/534 |
| 5,353,793 A | * | 10/1994 | Bornn | 600/386 |
| 5,913,830 A | * | 6/1999 | Miles | 324/207.16 |
| 6,047,203 A | * | 4/2000 | Sackner et al. | 600/301 |

* cited by examiner

*Primary Examiner*—Max F. Hindenburg
*Assistant Examiner*—Navin Natnithithadha
(74) *Attorney, Agent, or Firm*—Pennie & Edmonds LLP

(57) ABSTRACT

The present invention relates to the field of ambulatory and non-invasive monitoring of a plurality of physiological parameters of a monitored individual. The invention includes a physiological monitoring apparatus with an improved monitoring apparel worn by a monitored individual, the apparel having attached sensors for monitoring parameters reflecting pulmonary function, or parameters reflecting cardiac function, or parameters reflecting the function of other organ systems, and the apparel being designed and tailored to be comfortable during the individual's normal daily activities. The apparel is preferably also suitable for athletic activities. The sensors preferably include one or more ECG leads and one of more inductive plethysmographic sensor with conductive loops positioned closely to the individual to preferably monitor at least basic cardiac parameters, basic pulmonary parameters, or both. The monitoring apparatus also includes a unit for receiving data from the sensors, and for storing the data in a computer-readable medium. The invention also includes systems comprising a central data repository for receiving, storing, and processing data generated by a plurality of physiological monitored apparatus, and for making stored data available to the individual and to health care providers.

66 Claims, 10 Drawing Sheets

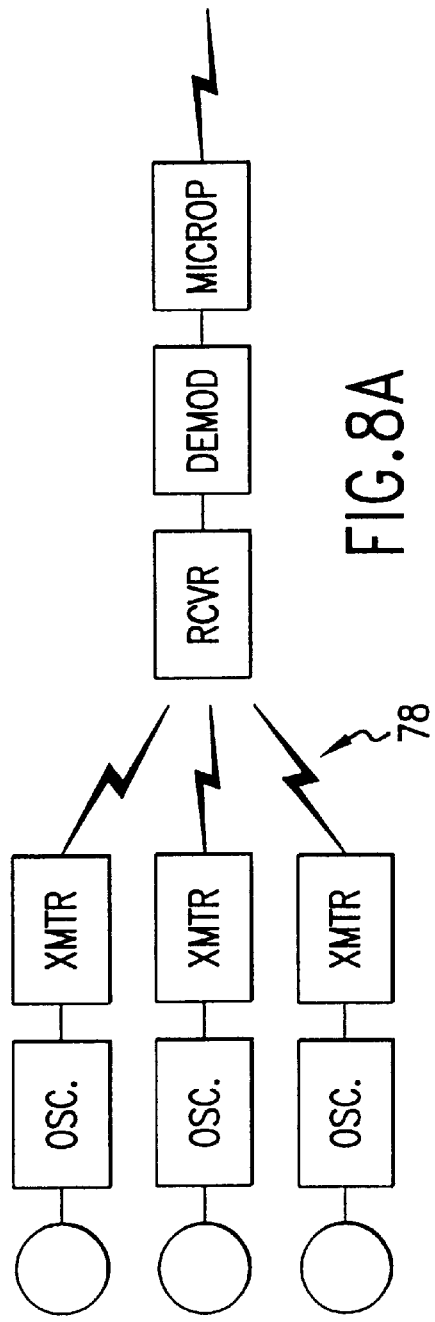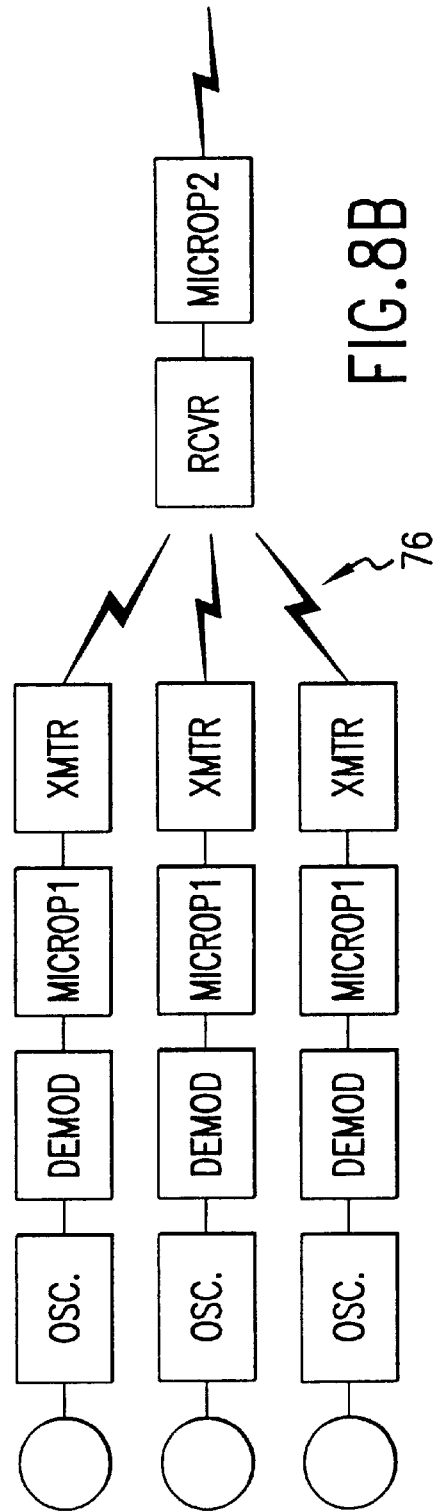

SYSTEMS AND METHODS FOR AMBULATORY MONITORING OF PHYSIOLOGICAL SIGNS

This application claims the benefit of Provisional application Ser. No. 60/197,589, filed Apr. 17, 2000.

1. FIELD OF THE INVENTION

The present invention relates to the field of ambulatory and non-invasive monitoring of an individual's physiological parameters. In particular, the invention relates to a monitoring apparatus with an improved apparel worn by a monitored individual, the apparel having attached sensors for monitoring parameters reflecting pulmonary function, or parameters reflecting cardiac function, or parameters reflecting the function of other organ systems. The invention also includes systems for receiving, storing, and processing physiological-parameter data, and for making it available to the individual and to health care providers.

2. BACKGROUND OF THE INVENTION

In the following, the term "plethysmography" (and its derivative words) means measurement of a cross-sectional area of the body, such as a cross-sectional area of the chest or of the abdomen, or a body part, such as a cross-sectional area of the neck or of an arm. (This meaning is somewhat more limited than is standard in the medical arts.) Further, the phrase "inductive plethysmography" means herein plethysmographic measurements which depend on inductance determinations.

Measurement of pulmonary and cardiac physiological parameters by means of inductive plethysmography is known. For example, many measurement methods and apparatus are disclosed in the following U.S. patents, the entire disclosures of which are incorporated herein, in their entireties, by reference, for all purposes.

(1) The '872 patent: U.S. Pat. No. 4,308,872, issued Jan. 5, 1982 and titled "Method and Apparatus for Monitoring Respiration," discloses a method and apparatus for monitoring respiration volumes by measuring variations in the patient's chest cross sectional area, or variations in both chest and abdomen cross sectional areas, each area being measured by determining the inductance of an extensible electrical conductor closely looped around the body, and the measurements being calibrated by measuring the area variations for a few breaths while directly measuring corresponding volumes of breath, preferably while the patient assumes at least two body positions, for example sitting and supine.

(2) The '534 patent: U.S. Pat. No. 4,373,534, issued Feb. 15, 1983 and titled "Method and Apparatus for Calibrating Respiration Monitoring System," discloses methods and systems in which respiration volume is determined by weighting signals representing abdominal and chest cross-sectional areas, where the weighting factors are determined by a procedure involving measuring respiration volume by an alternate measuring apparatus along with unweighted chest and abdomen signals, the measurements occurring for a first series of breaths based with a first relative chest and abdominal contribution and for a second series of breaths based on a second relative chest and abdominal contribution.

(3) The '252 patent: U.S. Pat. No. 4,452,252, issued Jun. 5, 1984 and titled "Non-invasive Method for Monitoring Cardiopulmonary Parameters," discloses a method for monitoring cardiopulmonary events by inductive plethysmographic measurement of a cross-sectional area of the neck, and further discloses a method for monitoring mouth volume by inductive plethysmographic measurement of a cross-sectional area of the head in a plane which extends through the mouth.

(4) The '015 patent: U.S. Pat. No. 4,456,015, issued Jun. 26, 1984 and titled "Non-invasive Method for Semiquantitative Measurement of Neck Volume Changes," discloses a method of plethysmographic measurement of a subject's neck volume by providing an extensible conductor closely circling the neck and, first, calibrated against cross-sectional area so that neck volume may be determined from the conductor's inductance, and also, second, calibrated against invasively-measured intrapleural pressure so that the intrapleural pressure may also be determined from the conductor's inductance, and also so that intrapleural pressure may also be obtained from measured neck volume.

(5) The '407 patent: U.S. Pat. No. 4,648,407, issued Mar. 10, 1987 and titled "Method for Detecting and Differentiating Central and Obstructive Apneas in Newborns," disclosing methods for detecting the presence and origin of apnea in newborns by concurrently monitoring relative movement of the cranial bones (which have been found to move with respiration as a function of intrapleural pressure), preferably by a surface inductive plethysmographic transducer, and nasal ventilation, preferably by a nasal cannula, thermistor, thermocouple or $CO_2$ sensor, wherein absence of changes in both cranial bone movement and respiratory air flow at the nose indicates of the presence of central apnea, while absence of nasal air flow accompanied by continuing cranial bone movements indicates of obstructive apnea.

(6) The '962 patent: U.S. Pat. No. 4,777,962, issued Oct. 18, 1988 and titled "Method and Apparatus for Distinguishing Central Obstructive and Mixed Apneas by External Monitoring Devices Which Measure Rib Cage and Abdominal Compartmental Excursions During Respiration," discloses an apparatus and method for distinguishing between different types of apneic episodes. The method includes measuring a new index, Total Compartmental Displacement/ Tidal Volume (TCD/VT), and measuring the phase relation between the abdominal and rib cage contributions to total respiration volume, wherein an episode is classified as central, obstructive or mixed based on the value of TCD/VT and the phase relation.

(7) The '640 patent: U.S. Pat. No. 4,807,640, issued Feb. 28, 1989 and titled "Stretchable Band-type Transducer Particularly Suited for Respiration Monitoring Apparatus," discloses an improved, low-cost stretchable band incorporating a conductor for disposition about the human torso or other three dimensional object, and particularly intended for use with respiration monitoring by means of inductive plethysmography, a method for making the band, which method is suitable to mass production techniques, and an improved enclosure housing circuitry releasably connected to the conductor in the band when the band is incorporated in respiration monitoring apparatus.

(8) The '473 patent: U.S. Pat. No. 4,815,473, issued Mar. 28, 1989 and titled "Method and Apparatus for Monitoring Respiration," discloses a method and apparatus for monitoring respiration volumes by inductive plethysmographic measurement of variations in a patient's chest cross sectional area, or preferably, variations in both chest and abdomen areas during breathing, and a method for calibrating such an apparatus by measuring cross-sectional area variations for a few breaths while directly measuring corresponding volumes of breath, preferably while the patient assumes at least two body positions, for example sitting and supine.

***(9) The '766 patent: U.S. Pat. No. 4,860,766, issued Aug. 29, 1989 and titled "Noninvasive Method for Measuring and Monitoring Intrapleural Pressure in Newborns," discloses measuring intrapleural pressure of a newborn subject by detecting relative movement between adjacently-proximate cranial bones, preferably, using a surface inductive plethysmographic transducer secured on the subject's head across at least two adjacently-proximate cranial bones, and a method of calibrating such measurements by temporarily manually occluding the subject's nose or, if intubated, the endotracheal tube, to measure the airway pressure during such occlusion as the subject makes an inspiratory effort and comparing the measured pressure to the measured signal.

(10) The '109 patent: U.S. Pat. No. 4,834,109, issued May 30, 1989 and titled "Single Position Non-invasive Calibration Technique," discloses an improved method for calibrating inductive plethysmographic measurement of respiration volume by totaling, during a period of breathing, a plurality of values of a parameter indicative of the relative amplitude, for each breath, of uncalibrated rib cage and abdomen signals, and by dividing the average variability of the means of the total of the values of one of the rib cage and abdomen signals by the average variability of the mean of the total of the values of the other signal, the quotient being so derived represents a signal weighting factor for determining respiration volume.

(11) The '277 patent: U.S. Pat. No. 4,986,277, issued Jan. 22, 1991 and titled "Method and Apparatus for Non-invasive Monitoring of Central Venous Pressure," discloses a method and apparatus for measuring central venous pressure (CVP) and changes in CVP along with an improved transducer (50) for measuring CVP in infants, wherein a plethysmographic transducer is disposed on the neck of a subject (or on the head in the case of infants), the signal from the transducer is processed to obtain a cardiac component, and the vertical distance from the transducer to a reference level is adjusted until a position is located at which the signal changes between a venous configuration and an arterial or mixed venous-arterial configuration, at which position the vertical distance approximates CVP.

(12) The '540 patent: U.S. Pat. No. 5,040,540, issued Aug. 20, 1991 and titled "Method and Apparatus for Non-invasive Monitoring of Central Venous Pressure, and Improved Transducer Therefor," discloses an improved method and apparatus for measuring central venous pressure (CVP), and changes in CVP, along with an improved transducer for measuring CVP in infants.

(13) The '935 patent: U.S. Pat. No. 5,159,935, issued Nov. 3, 1992 and titled "Non-invasive Estimation of Individual Lung Function," discloses a non-invasive method and apparatus for plethysmographic monitoring individual lung function by disposing a transducer on the torso above the lung to be monitored, the transducer producing a signal corresponding to movement of the torso portion there beneath which, in turn, corresponds to changes in the volume of the underlying lung, and also a method and apparatus for monitoring regional lung volume changes by utilizing transducers positioned on the torso to encompass only a portion of the underlying lung.

(14) The '151 patent: U.S. Pat. No. 5,178,151, issued Jan. 12, 1993 and titled "System for Non-invasive Detection of Changes of Cardiac Volumes and Aortic Pulses," discloses a method and an apparatus therefor for monitoring cardiac function in an animal or human subject including the steps of placing a first movement detecting transducer on the torso, said transducer overlying at least part of two diametrically opposed borders of the heart or great vessels; generating a signal indicative of the movement of the torso portion subtended by the transducer, said signal including a cardiac component comprising at least a segmental ventricular volume waveform or a segmental aortic pressure pulse waveform and assessing cardiac function by monitoring changes in said ventricular volume waveform or said aortic pressure pulse waveform.

(15) The '678 patent: U.S. Pat. No. 5,301,678, issued Apr. 12, 1994 and titled "Stretchable Band-Type Transducer Particularly Suited for Use with Respiration Monitoring Apparatus," an improved, low-cost stretchable band incorporating a conductor for disposition around the human torso or other three-dimensional object, and particularly intended for use with plethysmographic respiration monitoring apparatus, is disclosed.

(16) The '968 patent: U.S. Pat. No. 5,331,968, issued Jul. 26, 1994 and titled "Inductive Plethysmographic Transducers and Electronic Circuitry Therefor," discloses an apparatus and method for improving the detection of the inductance "signal" generated by an inductive plethysmograph by modifying the design of the inductive plethysmograph and also by improving the design of the associated circuitry, both of which permit the associated circuitry may be located remotely rather than on the transducer, the improvement including selecting the impedance matching transformer joining an inductive plethysmograph to an oscillator such that the inductance of its primary winding is greater than about ten times the reflected inductance of the inductive plethysmograph and the cable joining it to the transformer, or circling the conductor of the inductive plethysmograph therein around the relevant body portion a plurality of times, or selecting the cable connecting the inductive plethysmograph to the transformer such that the ratio of the diameter of its screen to the diameter of its center conductor is minimized for reducing the inductance per unit length thereof.

(17) The '425 patent: U.S. Pat. No. 5,588,425, issued Dec. 31, 1996 and titled "Method and Apparatus for Discriminating Between Valid and Artifactual Pulse Waveforms in Pulse Oximetry," discloses a method and apparatus for use in pulse oximetry for discriminating between valid pulse waveforms, determined with a photoelectric plethysmograph, from which arterial oxygen saturation levels are accepted, and artifactual pulse waveforms, from which saturation levels are rejected, according to whether the systolic upstroke time of each pulse waveform is within a predetermined range, it having been discovered that systolic upstroke times for valid pulse waveforms are in a consistent, narrow range which varies only slightly from subject to subject and which may be defined empirically for each subject or established by a default setting applicable to all subjects,

(18) The '388 patent: U.S. Pat. No. 6,015,388, issued Jan. 18, 2000 and titled "Method for Analyzing Breath Waveforms as to Their Neuromuscular Respiratory Implications," discloses a method for measuring respiratory drive by determining a peak inspiratory flow and a peak inspiratory acceleration from a breath waveform derived from rib cage motion and abdominal motion measured by external respiratory measuring devices, such as those based on inductive plethysmography, the measured respiratory drive being usable to initiate inspiration by a mechanical ventilator and for determining an index describing a shape of the waveform for controlling a continuous positive air pressure (CPAP) device.

(19) The '203 patent: U.S. Pat. No. 6,047,203, issued Apr. 4, 2000 and titled "Physiologic Signs Feedback System,"

discloses a non-invasive physiologic signs monitoring device which includes a garment, in a preferred embodiment, a shirt, with electrocardiogram electrodes and various inductive plethysmographic sensors sewn, embroidered, embedded, or otherwise attached to the garment with an adhesive, signals generated by the sensors being transmitted to a recording/alarm device where they are logged and monitored for adverse or other preprogrammed conditions, which is signaled by When an adverse condition or other preprogrammed condition occurs, a message is communicated to the patient by either an audio message or a display. The recording/alarm unit is also connectable to a remote receiving unit for monitoring by a health care professional or other machine.

However, nowhere in the art of inductive plethysmography are found teachings of practical and effective apparatus for non-invasive, ambulatory monitoring, of pulmonary and cardiac parameters. Such practical and effective monitoring apparatus would be of great benefit by assisting the transfer of health care from traditional hospital-based care, which is administered by trained health care workers, to home-based self care, which is administered by the individual patient during, if possible, the patient's normal daily activities. This transfer in health care has been found socially desirable because it may reduce health care costs and may increase patient involvement in and commitment to their treatment plans. Non-invasive and ambulatory monitoring apparatus may assist this transfer, because it eliminates the risks associated with invasive sensors placed within the body, such as intravascular catheters, risks which are considerably heightened outside of the hospital.

Citation or identification of any reference in this Section, including the patents listed above, or in any section of this application shall not be construed that such reference is available as prior art to the present invention.

3. SUMMARY OF THE INVENTION

The present invention has for its objects practical and effective apparatus for non-invasive and ambulatory monitoring of key pulmonary and cardiac parameters along with a system that may be used for interpretation and use of monitoring data to improve health care outcomes and to reduce health case costs. In preferred embodiments, the preferred apparatus is a garment which, while including inductive plethysmographic and other physiologic sensors, is sufficiently comfortable and unobtrusive to be worn for most activities of daily life.

In more detail, in a first embodiment, the present invention includes a monitoring apparatus for non-invasively monitoring physiological parameters of an individual comprising: a monitoring garment comprising a shirt for the torso of the individual to be monitored, one or more inductive plethysmographic (IP) sensors, each IP sensor comprising an inductance sensor including at least one conductive loop arranged to closely encircle the torso, wherein the inductance of the conductive loop is responsive to the cross-sectional area of the torso enclosed by the loop, a cardiac cycle sensor for generating signals responsive to occurrence of cardiac ventricular contractions, a signal cable for carrying signals from the sensors, and a microprocessor unit comprising a microprocessor for receiving signals from the signal cable and for recording digital data derived from all received signals in a removable computer-readable memory media.

In first aspects of the first embodiment, the cardiac cycle sensor comprises at least one electrocardiogram (ECG) electrode attached to the individual to be monitored; the cardiac cycle sensor comprises at least one IP sensor closely fitting about the neck of the individual to be monitored, wherein signals the inductance of the IP sensor is responsive to cardiac ventricular contractions because the cross-sectional area of the neck is responsive to carotid artery pulsations generated by cardiac ventricular contractions and the inductance of the IP sensor is responsive to the cross-sectional area of the neck; the computer-readable medium comprises a magnetic disk; the computer-readable medium comprises a flash memory module (64 MB or more).

In second aspects of the first embodiment, the monitoring garment further comprises a band for the neck of the individual to be monitored, and the IP sensors comprise a neck inductive plethysmographic sensor operatively arranged for generating signals responsive to jugular venous pulse, carotid arterial pulse, respiration-related intra-pleural pressure changes, contraction of neck muscles, and swallowing deflections, and the signal cable further comprises an attachment to the conductive loop of the neck IP sensor; the IP sensors comprise at least one abdominal IP sensor including one or more conductive loops and at least one rib cage IP sensor including one or more conductive loops operatively arranged for measuring breathing patterns of the patient; the IP sensors comprise at least one thoracic IP sensor including a two or more conductive loops operatively arranged for measuring ventricular stroke volume; the IP sensors comprise at least one lower abdominal IP sensor operatively arranged for measuring intra-lower-abdominal contractions and dilations; the IP sensors comprise at least one two hemithoracic IP sensors operatively arranged for measuring breathing and paradoxical motion between two hemithoraces of the patient.

In third aspects, the first embodiment further comprises one or more further sensors attached to the signal cable and selected from a group comprising a body position sensor for indicating a posture of the individual, a pulse oximeter for indicating arterial oxygenation saturation, and a throat microphone for indicating talking and snoring; or at least two body position sensors, a first body position sensor mounted on the garment and a second body position sensor mounted on a thigh of the individual; and the IP inductive plethysmographic sensors are attached to the garment as an integral part of the garment via an attachment consisting of one of sewing, embroidering, embedding, weaving and printing the inductive plethysmographic sensor into the garment; the microprocessor unit further comprises an audio device for generating audio indications to the individual being monitored; the microprocessor unit further comprises a display unit for displaying viewable messages to the individual being monitored; the microprocessor unit further comprises an input unit for the individual being monitored to input information or commands to the microprocessor unit.

In fourth aspects of the first embodiment, the microprocessor unit further comprises a memory accessible to the microprocessor, and wherein the memory comprises encoded software instructions for causing the microprocessor to read input data and to write output data derived from the input data in the removable computer-readable memory media; the memory further comprises encoded software instructions for causing the microprocessor to determine significant physiological events in the individual being monitored and to indicate audibly determined significant events to the individual; the microprocessor unit comprises components for wirelessly transmitting determined events and the memory further comprises encoded software instructions for causing the microprocessor to determine significant temporal physiological trends in the individual being monitored and to indicate audibly determined significant trends to the individual; the microprocessor unit comprises components for wirelessly transmitting determined significant trends; the memory further comprises encoded software instructions for causing the microprocessor to compress data before writing to the removable computer-readable memory media.

In fifth aspects of the first embodiment, the microprocessor unit further comprises circuitry for deriving digital data from non-digital data received from the signal cable; the monitoring apparatus further comprises circuitry for generating a variable-frequency signal from each IP sensor, the generated frequency being responsive to the inductance of the conductive loop of the IP sensor, and wherein the microprocessor unit further comprises circuitry for deriving digital data from the generated variable-frequency signals, the digital data comprising encoding of the variable frequency of the signals with errors of 100 ppm or less.

In a second embodiment, the present invention includes a monitoring apparatus for non-invasively monitoring physiological parameters of an individual comprising: a monitoring garment comprising a shirt for the torso of the individual to be monitored, one or more inductive plethysmographic (IP) sensors, each IP sensor comprising (i) a longitudinal band of elastic material attached to the garment for closely encircling the torso, (ii) an inductance sensor including at least one flexible conductive loop attached to the longitudinal band, wherein the inductance of the conductive loop is responsive to the cross-sectional area of the torso enclosed by the loop, and (iii) a tightening device for adjusting circumferential tightness of the IP sensor to substantially prevent longitudinal movement of the IP sensor along the torso, and a microprocessor unit comprising a microprocessor for receiving signals from the IP sensors and for recording digital data derived from all received signals in a removable computer-readable memory media.

In first aspects of the second first embodiment, longitudinal motion of each IP sensor is substantially prevented when the physiological parameters indicated by the inductance of the conductive loop of the sensor do not measurably change; the monitoring garment comprises excess fabric arranged to permit longitudinal stretching of the torso without applying force to the IP sensors sufficient to cause substantial longitudinal motion; longitudinal motion of each IP sensor is substantial if physiological parameters indicated by the inductance of the conductive loop of the sensor change as the monitoring garment is worn by the individual; the monitoring garment comprises fabric with sufficient longitudinal elasticity to permit longitudinal stretching of the torso without applying force to the IP sensors sufficient to cause substantial longitudinal motion.

In second aspects of the second embodiment, the tightening device comprises a cinch band and a gripping device for releasably gripping excess cinch band under tension; the tightening device comprises a drawstring;

In third aspects, the second embodiment, comprises a cardiac timing sensor for generating signals responsive to cardiac ventricular contractions, and wherein the microprocessor unit further records digital data derived from signals received from the cardiac timing sensor; or a signal cable for carrying signals from the sensors to the microprocessor unit.

In a third embodiment, the present invention includes a monitoring apparatus for non-invasively monitoring physiological parameters of an individual comprising: a monitoring garment comprising a shirt for the torso of the individual to be monitored and a longitudinal fastener for opening and closing the shirt, one or more inductive plethysmographic (IP) sensors, each IP sensor comprising an inductance sensor including at least one flexible conductive loop arranged to closely encircle the torso, wherein the inductance of the conductive loop is responsive to the cross-sectional area of the torso enclosed by the loop, a cardiac timing sensor for generating signals responsive to occurrence of cardiac ventricular contractions, a signal cable for carrying signals from the sensors comprising at least one module, wherein the module is coupled to and electrically completes the conductive loops of the IP sensors, wherein termini of the conductive loops may be uncoupled from module, and wherein the module comprises circuitry for generating signals responsive to the IP sensors, and a microprocessor unit comprising a microprocessor for receiving signals from the signal cable and for recording digital data derived from all received signals in a removable computer-readable memory media.

In first aspects of the third embodiment, at least one IP sensor further comprises a tightening device for adjusting circumferential tightness of the IP sensor to substantially prevent longitudinal movement of the IP sensor along the torso, and wherein the tightening device can be arranged not to impede unfastening of the shirt; the conductive loops of the IP sensors and the module further comprise mating connectors so that the conductive loops may be connected and disconnected from the module; the signals generated by the module in response to each IP sensor comprise digital data encoding the frequency of an oscillator responsive to the inductance of the conductive loop of the IP sensor, the frequency being encoded with errors of 100 (or 10) ppm or less;

In second aspects of the third embodiment, the signals generated by the module in response to each IP sensor comprise signals of variable frequency, the frequency being responsive to the inductance of the conductive loop of the IP sensor; the microprocessor unit further comprises circuitry for deriving digital data from the variable-frequency signals generated from each IP sensor, the digital data comprising encoding of the variable frequency of the signals with errors of 100 ppm or less; the microprocessor unit further comprises multiplex circuitry for permitting single deriving circuitry to derive digital data from a plurality of variable-frequency signals.

In a fourth embodiment, the present invention includes a monitoring apparatus for non-invasively monitoring physiological parameters of an individual comprising: a monitoring garment comprising a shirt for the torso of the individual to be monitored, one or more inductive plethysmographic (IP) sensors, each IP sensor comprising an inductance sensor including at least one flexible conductive loop arranged to closely encircle the torso, wherein the inductance of the conductive loop is responsive to the cross-sectional area of the torso enclosed by the loop, a cardiac timing sensor for generating signals responsive to occurrence of cardiac ventricular contractions, a signal cable for carrying signals directly from the conductive loops of the IP sensors and for carrying signals from the sensor, electronic circuitry comprising (i) a multiplexing switch for connecting the conductive loop of any one of the IP sensors to an oscillator, the oscillator having an oscillation frequency responsive to the inductance of the conductive loop connected by the multiplexing switch, and (ii) a demodulator operatively coupled to the oscillator and outputting digital data responsive to the oscillation frequency, and a microprocessor unit comprising a microprocessor for receiving signals from the signal cable and for receiving digital data from the electronic circuitry and for recording digital data from received inputs in a removable computer-readable memory media.

In first aspects of the fourth embodiment, the digital data responsive to the oscillation frequency has errors of 100 (or 10) ppm or less; the electronic circuitry is housed in the microprocessor unit; the resistance of the data signal cables and the multiplexing switch from the conductive loop of any IP sensor to the oscillator is less than 1 Ω; the multiplexing switch is controlled so that oscillator is periodically connected to the conductive loop of each IP sensor for the duration of a sampling period (1 msec or less).

In second aspects of the fourth embodiment, the digital data output by the demodulator comprises digital data encoding a count of a number cycles of the oscillator occurring within a sampling period and digital data encoding a count of a number of periods of a clock occurring within the counted oscillator cycles; the microprocessor unit further comprises a memory accessible to the microprocessor, and wherein the memory comprises encoded software instructions for causing the microprocessor to determine the actual oscillator frequency by dividing the count of the number of oscillator cycles by the count of the number of clock periods; the memory further comprises software instructions for causing the microprocessor to determine an more accurate frequency by combining the counts of a plurality of sampling periods.

In a fifth embodiment, the present invention includes a monitoring apparatus for non-invasively monitoring physiological parameters of an individual comprising: a monitoring garment comprising a shirt for the torso of the individual to be monitored, a plurality of sensors, the sensors comprising (i) one or more inductive plethysmographic (IP) sensors, each IP sensor comprising an inductance sensor including at least one flexible conductive loop arranged to closely encircle the torso, wherein the inductance of the conductive loop is responsive to the cross-sectional area of the torso enclosed by the loop wherein at least one sensor comprises a transmitter for wirelessly transmitting signals generated by the sensor within the vicinity of the physiological monitoring apparatus, a microprocessor unit comprising (i) a receiver for receiving signals wirelessly transmitted from the sensors, and (ii) a microprocessor for accepting the received signals and for recording digital data derived from the received signals in a removable computer-readable memory media.

In first aspects of the fifth embodiment, at least one sensor generates output signals in a digital form, and wherein the transmitter transmits the generated digital signals; the transmitter and the receiver conform to the Bluetooth standard; at least one sensor generates variable-frequency analog output signals, and wherein the transmitter output is modulated by generated variable-frequency analog signal; all sensors comprise a transmitter for wirelessly transmitting signals generated by the sensor within the vicinity of the physiological monitoring apparatus.

In second aspects, the fifth embodiment further comprises a signal cable, wherein the output of at least one sensor is carried to the microprocessor unit by a signal cable, and wherein the microprocessor records digital data derived from signals carried by the signal cable; the sensors further comprise a cardiac timing sensor for generating signals responsive to occurrence of cardiac ventricular contractions.

In a sixth embodiment, the present invention includes a system for the non-invasive physiological monitoring of physiological parameters of at least one individual comprising: at least one physiological monitoring apparatus comprising a monitoring garment worn on the torso of an individual being monitored, wherein the monitoring apparatus stores in a digital form in a removable computer-readable memory media data, wherein the data is by sensors comprising generated from (i) one or more inductive plethysmographic (IP) sensors flexibly attached to the monitoring garment, and (ii) a cardiac timing sensor for generating signals responsive to cardiac ventricular contractions, and a data repository for reading data from the removable computer-readable memory media that has been recorded by the physiological monitoring apparatus and for storing read data in a data archive, the data repository being remotely located from the physiological monitoring apparatus.

In first aspects of the sixth embodiment, the physiological monitoring apparatus further transmits data wirelessly, and wherein the data repository further receives data wirelessly that has been transmitted by the physiological monitoring apparatus, and then stores the received data; the physiological monitoring apparatus further comprises a microprocessor for processing the generated data for determining physiological events and alarms, and wherein the data wirelessly transmitted comprises the determined physiological events and alarms.

In second aspects, the sixth embodiment further comprises a local data repository co-located with the physiological monitoring apparatus, wherein the local data repository receives data wirelessly transmitted by the physiological monitoring apparatus and stores received data in a local data archive, and wherein the local data repository comprises display terminals for making stored data available to local health care professionals; the data repository further comprises display terminals for making stored data available to health care professionals and to users monitoring the operation of the system.

In third aspects, the sixth embodiment, further comprises a plurality of physiological monitoring apparatus, each apparatus for monitoring a different individual, and wherein the data repository reads data from removable computer-readable memory media recorded by the plurality of physiological monitoring apparatus.

In a seventh embodiment, the invention further includes a computer readable medium comprising data recorded in digital form, wherein the recorded digital data comprises data responsive with errors of 100 ppm or less to the frequency of an oscillator connected to at least one conductive loop of at least one inductive plethysmographic sensor; and also encoded software for causing microprocessors, data repositories, and the like to perform the described methods.

4. BRIEF DESCRIPTION OF THE FIGURES

The present invention may be understood more fully by reference to the following detailed description of the preferred embodiment of the present invention, illustrative examples of specific embodiments of the invention and the appended figures in which.

Figure 7:
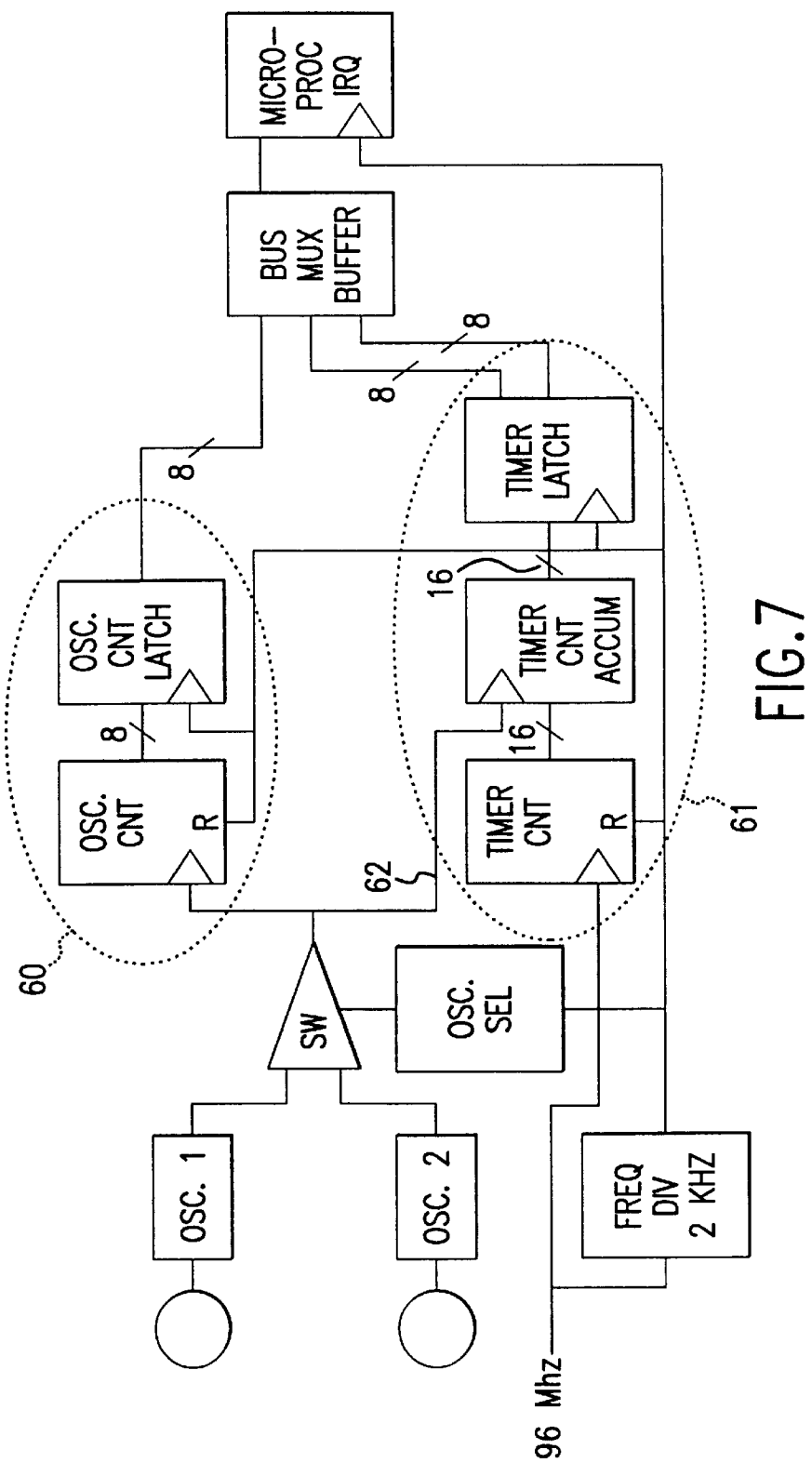
Figure 9:
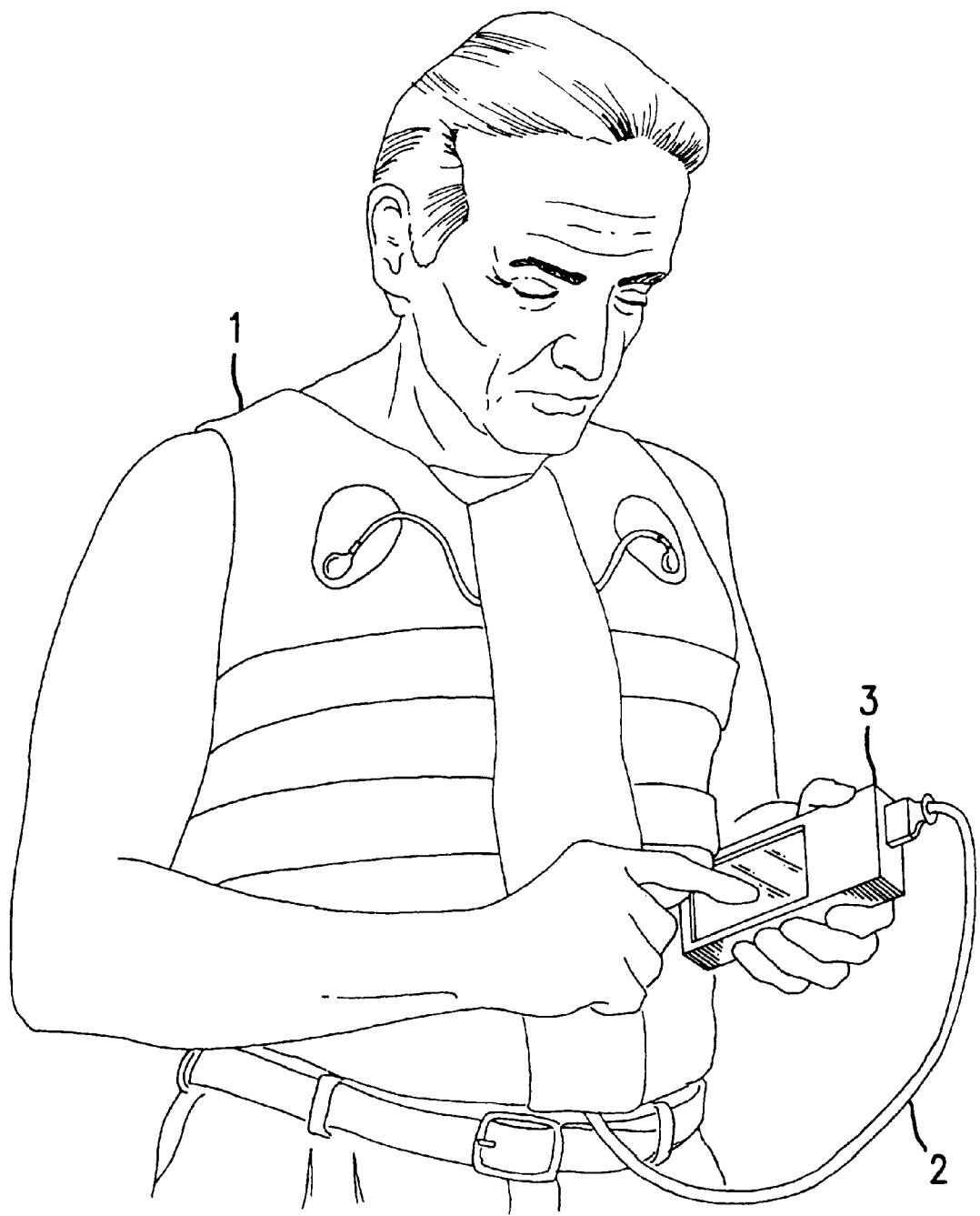
Figure 10:
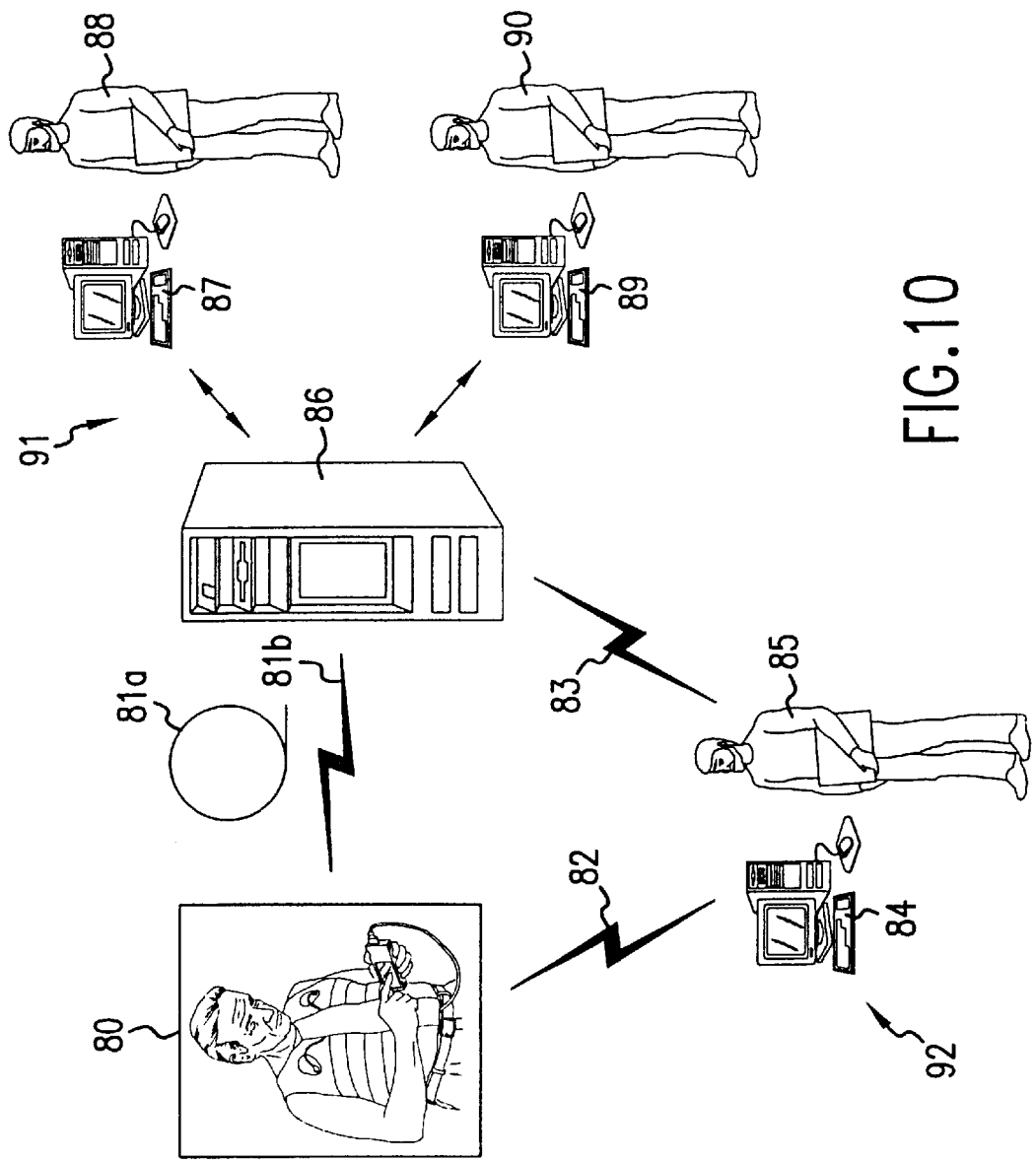

FIGS. 6A–C illustrate alternative functional distributions of inductive-plethysmographic signal processing;

FIG. 7 illustrates demodulator processing;

FIGS. 8A–B illustrate alternatives for wireless transmission within an individual's monitoring apparatus;

FIG. 9 illustrates a particular embodiment of the monitoring apparatus of the present invention; and FIG. 10 illustrates a system according to the present invention.

5. DETAILED DESCRIPTION OF THE PREFERRED EMBODIMENT

This section begins with an introductory description of inductive plethysmography, its physiological applications, and its measurement requirements. After the introduction are detailed descriptions of this invention's practical and effective apparatus for non-invasive, ambulatory monitoring, of pulmonary and cardiac parameters, which in preferred embodiments are various garments incorporating inductive plethysmographic sensors.

5.1. Inductive Plethysmograph

"Inductive plethysmography" means herein measurement of a cross-sectional area of the body by determining the self-inductance of a flexible conductor closely encircling the area to be measured. Since the inductance of a substantially planar conductive loop is well known to vary as, inter alia, the cross-sectional area of the loop, a inductance measurement may be converted into a plethysmographic area determination. Varying loop inductance may be measured by techniques known in the art, such as, e.g., by connecting the loop as the inductance in a variable frequency LC oscillator, the frequency of the oscillator then varying with the cross-sectional area of the loop inductance varies. Oscillator frequency is converted into a digital value, which is then further processed to yield the physiological parameters of interest.

Specifically, a flexible conductor measuring a cross-sectional area of the body is closely looped around the area of the body so that the inductance, and the changes in inductance, being measured results from magnetic flux through the cross-sectional area being measured. The inductance thus depends directly on the cross-sectional area being measured, and not indirectly on an area which changes as a result of the factors changing the measured cross-sectional area.

Various physiological parameters of medical and research interest may be extracted from repetitive measurements of the areas of various cross-sections of the body. For example, pulmonary function parameters, such as respiration volumes and rates and apneas and their types, may be determined from measurements of, at least, a chest transverse cross-sectional area and preferably also and an abdominal transverse cross-sectional area (and optionally further cross-sectional areas). See, e.g., The '872 and '473 patents; see also, e.g., The '534, '252, '015, 962, '109, '935, and '388, which describe various calibration and processing techniques for respiratory-related inductive plethysmographic signals as well as extensions to measuring intra-pleural pressure and individual lung function, and the description following.

Cardiac parameters, such central venous pressure, left and right ventricular volumes waveforms, and aortic and carotid artery pressure waveforms, may be extracted from repetitive measurements of transverse cross-sectional areas of the neck and of the chest passing through the heart. See, e.g., The '277, '540, '151 patents. At least, the cross-sectional of a plane at about the position of the xiphoid process is measured. In order to easily extract cardiac data from variations in these cross-sectional areas, it is helpful to have concurrent measurements of cardiac timing, especially of the onset of left ventricular contraction. Timing measurements are preferably obtained from concurrent ECG measurements, and less preferably from the carotid pulse signal present in the neck. Note: In more detail, area measurements of transverse cross-sectional areas more inferiorly through the heart give stronger indications of left ventricular waveforms, while measurements of areas more superiorly through the heart give stronger indications of right ventricular waveforms. These cardiac signals may be more positively identified by correlation with pulmonary signals. Left ventricular waveforms typically have larger stroke volume on expiration than on inspiration, while right ventricular waveforms typically have the opposite pattern.

Further related parameters may be extracted from these and other signals. From the cardiac-related signals, indications of ischemia may be obtained independently of any ECG changes. Ventricular wall ischemia is known to result in paradoxical wall motion during ventricular contraction (the ischemic segment paradoxically "balloons" outward instead of normally contracting inward). Such paradoxical wall motion, and thus indications of cardiac ischemia, may be extracted from chest transverse cross-section area measurements. Left or right ventricular ischemia may be distinguished where paradoxical motion is seen predominantly in left or right ventricular waveforms, respectively. For another example, observations of the onset of contraction in the left and right ventricles separately may be of use in providing feedback to bi-ventricular cardiac pacing devices. For a further example, pulse oximetry determines hemoglobin saturation by measuring the changing infrared optical properties of a finger. This signal may be disambiguated and combined with pulmonary data to yield improved information concerning lung function. See, e.g., The '425 patent.

Determination of other physiological parameters by measurement of other cross-sectional areas is discussed subsequently.

Useful and effective determination of physiological parameters generally requires inductance measurements of sufficient accuracies at sufficient rates. First, in order to avoid interference using electronics of reasonable cost, it is preferable to measure loop inductance at a frequency which is otherwise relatively unused, or at least not likely to be encountered in most ambulatory settings. The preferred frequency is from about 200 kHz to about 400 kHz which is assigned to aeronautical and aeronautical marine navigation beacons and is below the standard AM broadcast band.

Next, necessary measurement accuracies may be determined from known electronic circuit laws combined with measured bodily displacements resulting from the physiological events being monitored. Measurement accuracies may also be simply determined from observation of particular measurement configuration. Using either approach, it has been determined that respiratory activity generally leads to frequency changes of 500–1000 ppm (parts per million). Cardiac activity generally leads to frequency changes of 50–100 ppm. Therefore, for monitoring both respiratory and cardiac activities, it is most preferably frequency measurements have an accuracy of less than 1–2 ppm, preferably less than 5 ppm, and less preferably less than 10 ppm (and at least less than 100 ppm).

Sufficient measurement rates for respiratory and cardiac activities are generally known in the art and have been confirmed and refined by observation. Generally, respiratory activity is preferably measured at approximately 50 Hz or more; cardiac activity (including cross-sectional areas and any accompanying ECG) preferably at approximately 200 Hz or more, and vascular activity (such as arterial or venous pulsation) preferably at 100 Hz or more.

Of course, particular monitoring tasks may require higher accuracies or rates, or may permit reduced accuracies or rates. Appropriate accuracies and rates may be easily determined by one of skill in the art in view of the monitoring task.

5.2. Preferred Apparatus

In the following, various particular aspects of the present invention are illustrated in various combinations. The illustrated combinations are intended to be exemplary and not to be limiting. One of skill in the art will recognize that these particular aspects, illustrated or not, may be combined in different combinations in order to respond to different monitoring tasks. For a simple example, pulmonary (or cardiac) sensors may be eliminated from a monitoring apparatus where only cardiac (or pulmonary) parameters are of interest. On the other hand, additional sensors may be added to the illustrated embodiments where called for.

5.2.1. Monitoring Garment and Sensors

FIG. 9 illustrates an embodiment of the monitoring apparatus present invention for monitoring basic pulmonary and cardiac parameters in an ambulatory setting of daily activity with minimum encumbrance to the individual being monitored and in an economical manner. This apparatus includes monitoring garment 1, sensor cabling 2, and microprocessor unit 3.

Figure 1:
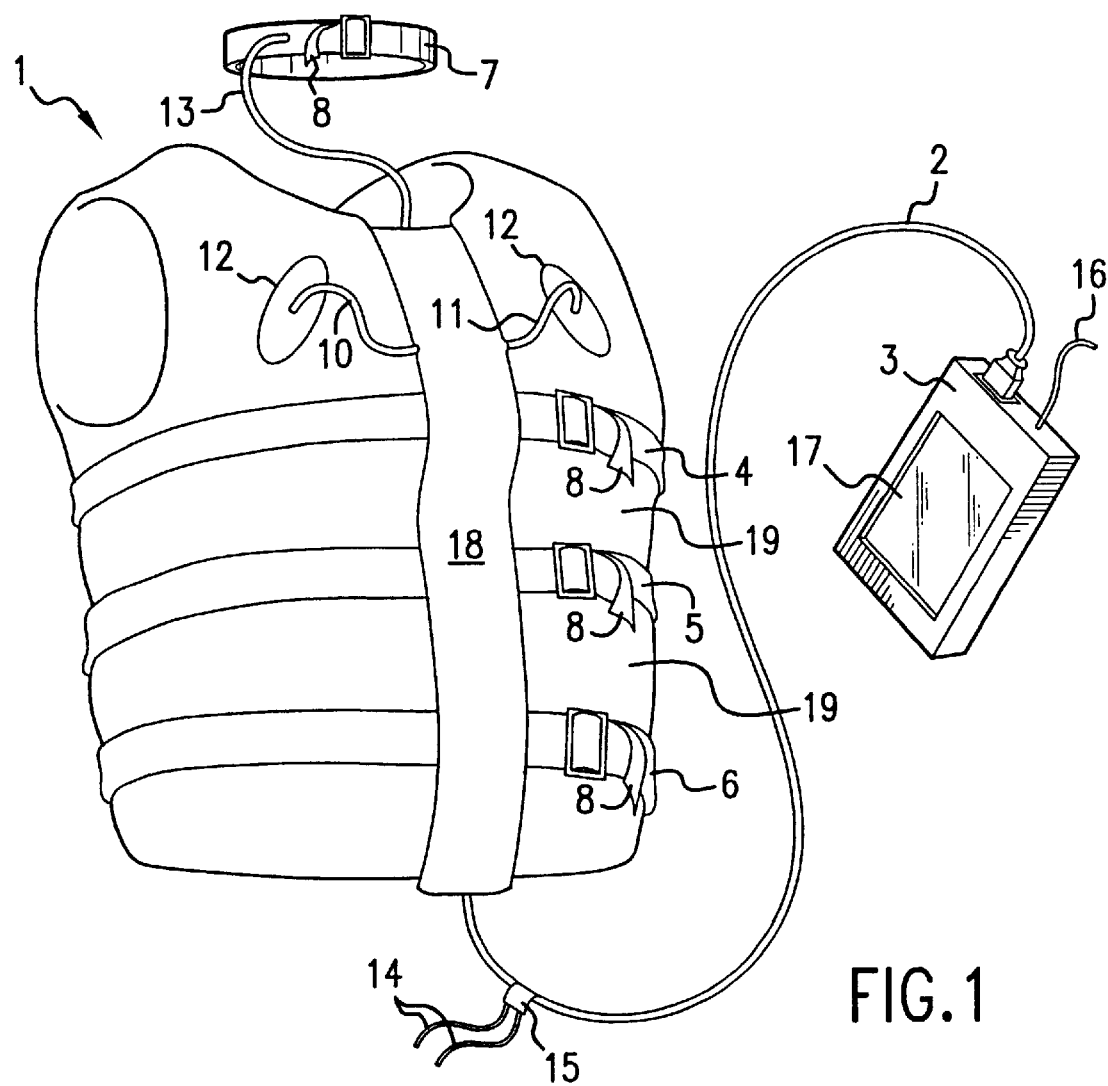
FIG. 1 illustrates a front view of a preferred monitoring apparatus constructed in accordance with to the present invention.

These components are next described in detail, beginning with FIG. 1. Monitoring garment 1 (FIG. 1) is generally in the form of a sleeveless shirt appropriate for a male of a stout habitus. Modifications of this garment so that it will appropriate for a male with a trimmer habitus, or for females of various habituses will be readily apparent to one of skill in the art. Alternatively, the garment may be of a cut and material so that, consistent with the requirements to be described, it will be appropriate for individuals of a range of body habituses and possible also for both sexes. In a further alternative, the garment may be made of an elastic material so that a single garment cut and size is able to fit a wide variety of individuals.

To measure basic pulmonary parameters, garment 1 is equipped with chest inductive plethysmographic sensor band 4 and abdominal inductive plethysmographic sensor band 6. Band 4 is preferably positioned just inferior to the axilla, and band 5 is preferably positioned 1 to 2 cm superior to the umbilicus. To measure basic cardiac parameters, garment 1 is equipped with thoracic inductive plethysmographic sensor band 5 and optional neck inductive plethysmographic sensor band 7, which is separate from garment 1. Band 5 is preferably positioned at the level of the xiphoid process, and band 7 is preferably positioned 1 to 2 cm superior to the base of the neck. Preferably, the garment has cutouts 12 for attaching ECG electrodes and ECG leads 10 (approximating right arm signals) and 11 (approximating left arm signals) and 12 (approximating left leg signals). In alternative embodiments, sensor bands 4 and 6 or sensor band 5 may be eliminated, or optional sensor band 7 may not be present, or additional sensor bands may be present, or so forth.

In this embodiment, signals from all the sensors mounted on or with the garment, including any ECG signals, are conducted to external microprocessor unit 3 via signal cable 2. Signal cable 2 is extended by optional signal cable 13 to conduct signals from optional neck band 7. Connections between signal cable 2 and the various sensors reside underneath openable flap 18, which both protects the connections and any electronic modules closely associated with the sensors from disruption or damage and also presents a more aesthetic surface appearance. In alternative embodiments, the signal cable may be attached to the garment by several snaps positioned or the like, associated electronic modules may be carried in pockets of the garment, and connections firmly held in place by mechanical means. Other manners for protectively securing the signal cable will be apparent to one of skill in the art and are within the scope of the present invention.

Also underneath the flap is a zipper, preferably the full length of the garment, to assist in placing and removing the garment. Alternatively, and less preferably, the garment may be arranged for placement and removal over the head in one piece. In this case, there is no need for a zipper or other fastening devices. Other similar garment fastening devices may be used, for example, a plurality of buttons and buttonholes, or a plurality of loops fitting into grommets, or a plurality of ties, or a zipper-like device with halves fitting together continuously instead of by a plurality of teeth. More than one zipper may also be used.

Inductive plethysmographic (IP) sensor bands 4, 5, 6, and 7 and the garment 1 itself preferably include several functional or structural elements to meet several conditions advantageous for good signal quality. First, the sensor bands include the sensors themselves, which are conductor loops around the body in the substantially transverse planes whose cross-sectional area is to be measured. Since the bands should remain in close circumferential contact to the torso (of the body of the individual to be monitored) in order to accurately sense cross-section areas that change during activity, the conductor should be longitudinally flexible to accommodate normal physiological movements. Further, to achieve sufficient measurement accuracy and rate, the LC circuit containing the conductor loop must have a sufficiently high Q factor. Generally, at the preferred frequencies, the conductors preferably have a resistance of less than approximately 1 $\Omega$ (Ohm). Any flexible low-resistance conductor may be used. In preferred embodiments, the conductor is metallic wire, sinusoidally arranged for expansion and contraction without hindrance of the cross sectional area to inductance relationship. For example, the sinusoidal wire arrangement may have an "amplitude" of 1 to 2 cm with "wavelength" adequate to provide for longitudinal flexibility sufficient to accommodate anticipated activity.

For chest sensor band 4 and abdominal sensor band 6, which obtain respiratory signals, generally one loop of conductor about the body achieves sufficient signal quality. For thoracic sensor band 5, and also for neck sensor band 7, several loops, generally from 2 to 4 loops, achieve sufficient signal quality.

Next, in order to remain in close circumferential contact to the body, it is preferable that the sensor bands also include an elastic material providing longitudinal elasticity sufficient to retain the band against the body. For example, the bands may include a longitudinally arranged strip of elastic material similar to that in elastic bandages well known in the art. The sensor conductors may attached by a plurality of distinct connections, which may be sewn loops of thread. More preferably, the bands may include a woven or knitted elastic material into which sinusoidally arranged copper wire is integrally included during the weaving or knitting process. See, e.g., U.S. patent application Ser. No. 09/774,333, filed Jan. 31, 2001, and assigned to the assignee of the present application (included by reference herein in its entirety for all purposes). The sensor conductor may be attached to underlying material of other ways known in the art, for example, by glue.

In addition to simply remaining in close circumferential contact with the body, the bands should not move inferiorly or superiorly (collectively, longitudinally) over the surface of the torso of body, in other words, be longitudinally stable, during normal daily activities. This is advantageous so that signals from each band are responsive only to the one intended cross-sectional area. For a sufficiently trim male engaging only in light activity, the elasticity that keeps bands in close circumferential contact may be sufficient to achieve longitudinal stability. However, it has been discovered that generally, and especially for normal or vigorous activity, such as jogging or other athletic activities, or for individuals with a larger body habitus, this circumferential elasticity may not be sufficient for longitudinal stability.

Therefore, in the embodiment illustrated in FIG. 1, each band is also equipped with an individual tightening device 8, which permits individual adjustment of the tightness of each band as needed. One such tightening means, schematically illustrated by tightening device 8, is a gripping device in which metal or plastic teeth or paired rings grip excess material 8 attached to the band. Pulling excess material so that the gripping device holds the excess material under tension will tighten a band, while release of the mechanism (e.g., rings or teeth) of the gripping device loosens the bands for undressing. In this manner, after dressing in the monitoring garment, the bands can be individually adjusted to a tightness discovered to be sufficient after an initial period of monitoring garment use. The bands may be loosened or released in preparation for undressing. Preferably, the "excess" material and gripping device form a cinch (also known as a girth) in that the "excess" material is part of a band of material circling the patient included as part of the inductive plethysmographic sensor band assembly. Alternative tightening means include belt-buckle-like arrangements with a tooth for protruding through one of plurality of holes in the excess material, or a slidable spring-loaded device that grips the excess material against a grommet as used in a drawstring, or simply a bow-type knot used like a shoe lace, or other gripping means. Any cinch or girth material must of course also be elastic, but preferably stiffer (less elastic) than existing sensor band material.

One aspect of longitudinal stability is that during activity the garment material itself may pull on the bands causing mechanical coupling both of a band sensor to a more extended longitudinal region than intended and also between adjacent, separate band sensors. This coupling may mix decrease signal specificity, and may mix together signals from the so-coupled sensors leading to decreased accuracy of physiological parameter determination, or even an inability to determine certain parameters. Therefore, it may be advantageous for the garment material between the sensor bands not to be tight, but rather have an excess sufficient to accommodate longitudinal stretching and other longitudinal motions that accompany activities of all expected degrees of strenuousness. (For example, such excess material may be present in regions 19 of garment 1 of FIG. 1.) Alternatively, the garment material may be sufficiently stretchable in a longitudinal and the bands sufficiently elastic to be circumferentially tight, or synched to be sufficiently tight, so that longitudinal motions are accommodated mainly by stretching of the garment with little or no longitudinal band movement with respect to the torso. These designs may be combined so that the garment between the bands has some excess of an elastic material. In particular, where the garment is made of an elastic material to accommodate a range of body types, care must be taken to prevent longitudinal mechanical coupling occurring, especially for individuals of larger body types relative to the garment size and cut.

Where the garment is zippered, or otherwise similarly fastened, at least some of the inductive plethysmographic (IP) sensor bands are necessarily interrupted. However, the garment fasteners should be arranged such that, when the garment is fastened, circumferential band elasticity is established even though elastic in the sensor bands is necessarily interrupted at the garment division. With zippers, this is easily achieved because of the substantially continuous nature of a zipper fastener. Further any band tightening devices must also cooperate with the garment fasteners. With a cinch (or girth) held by a gripping device, this is easily achieved by allowing excess cinch to extend across the division in the garment. Lastly, the conductive loop is interrupted at the garment division, and may bridge this division by equipping ends of the loop with mating pair of a plug and a connector. Alternatively, one or both ends of the conductor bands may plug into connectors carried on the signal cable (see below). One of skill in the art will readily be able to similarly arrange the IP sensor bands for cooperation with other types of garment fasteners.

In addition to the sensors already described, additional sensors may be incorporated with monitoring apparatus of the present invention. For correctly interpreting physiological parameters obtained during ambulatory monitoring, it is advantageous to have information from which the posture of the patient can be determined. At least, it is useful to determine if the monitored individual is lying, sitting, or standing, and if standing, whether still, walking, or running. In a preferred embodiment, this information is provided by accelerometers that measure orientation with respect to gravity. The apparatus illustrated in FIG. 1 preferably includes an accelerometer attached to garment 1, optionally by being integrated into an electronic module associated with one of the band sensors. Such a single sensor can provide only the orientation of the torso. Further information may be provided by optional accelerometers strapped to one or both thighs. Signals from these additional accelerometers may be conducted to signal cable 2 by means of secondary cables 14, which attach to the signal cable at connector 15.

Further, any transdermal sensor may be incorporated into the illustrated monitoring apparatus. Such sensors may include pulse oximeters, which measure hemoglobin saturation in a finger, blood pressure sensors of various types, transdermal sensors indicative of blood chemistry, for example, blood glucose sensors or sweat electrolyte sensors, and so forth. Signals from these sensors may reach microprocessor module 17 over signal cable 16. Preferably, these sensors will present a standard interface to the microprocessor module, for example an RS-232 or more modem serial interface. Further, it may be advantageous to obtain more complete ECG information, such as by receiving signals from 7 or 12 leads placed in manners well known in the art. A further additional sensor may be a throat microphone, which is useful for detecting snoring during sleep and talking during wakefulness. Detection of snoring during sleep is a valuable indication of incipient or actual upper airway obstruction useful in sleep apnea studies. In such an embodiment, the microprocessor module may accumulate information reflecting a broad array of transdermally measurable physiological parameters in a scandalized ???manner and in a standardized format.

5.2.2. Microprocessor Unit and Cable

As described previously, the monitoring apparatus of this invention may be provided with primary and secondary signal cables. FIG. 1 illustrates primary signal cable 2 which carries signals from the primary sensor bands 4, 5, and 6, and secondary sensor band 7. This cable also has provision for carrying ECG signals, provided, for example, over leads 10 and 11, and provision for signals from other sensors received at connector 15. Further, secondary signal cable 16 may optionally carry signals from a number of other sensors arranged on the body.

Signals gathered by the monitoring apparatus are received by microprocessor unit 3. Unit 3 performs at least basic data entry and storage functions, and optionally performs alarm functions, communication functions, and power management functions. The unit may be built as an add-on to existing personal digital assistants (PDAs), cell phones, cell phone/PDA combinations, bidirectional pagers, especially those used for e-mail exchange, and other similar handheld devices. Also the unit may be a custom design including at least a microprocessor and associated components, and optionally signal processor circuits. Preferably, unit 3 has display screen 17 which is touch sensitive for data input by the monitored individual. Other user interface features may be provided, such as voice command recognition, voice or audible alarm output, attachable keyboard, and so forth. This unit may also optionally include wireless communication circuits. Also, although FIG. 1 illustrated unit 3 as possibly hand-held, it may also be carried on an individual normal clothing, for example, on a belt, or may be placed in a pocket provided on garment 1.

A first data entry function is to receive and store information input by a monitored individual. For example, a monitored individual may enter major activities during the day along with any symptoms that might be observed.

A second data entry and storage function, to receive and store digitized signals generated by the sensors of a monitoring apparatus of this invention, is closely linked with possible communication functions. Preferably, the present invention conforms to well known standards for "standard event recording" by advantageously and preferably storing all raw signal data, whether or not it is used only in summary form for health care personnel. Storing raw data in a central repository is encouraged by regulatory authorities, and is important in quality control of monitoring by the present invention. Further, health care personnel may from time-to-time wish to examine the raw data indicative of the physiological events occurring in the monitored individual, which is possible by accessing the central repository.

However, this raw data may be voluminous, even for a basic monitoring garment. Table I presents the data rates generated by the apparatus of FIG. 1 wherein operation is with preferred sample precision and data rate for each sensor.

TABLE I

Exemplary Data Rates

| Sensor | Bits per sample | Samples per second | Data rate (MB/hr) |
|---|---|---|---|
| Chest sensor band | 16 | 50 | 0.36 |
| Abdominal sensor band | 16 | 50 | 0.36 |
| Thoracic cardiac sensor band | 16 | 200 | 1.44 |
| Neck sensor band | 16 | 100 | 0.72 |
| Accelerometer | 8 | 10 | 0.04 |
| ECG | 12 | 200 | 1.08 |
| Pulse oximeter | 8 | 50 | 0.18 |
| Throat microphone | 8 | 10 | 0.04 |
| TOTAL | | | 4.22 |
| | | | (= 1.2 kbits/sec) |

Therefore, the present invention includes various tradeoffs for the storage or raw data, which depend primarily on available battery power and accessible wireless facilities. For example, if high bandwidth wireless data transfer, for example 64 kbits/sec or greater, is available throughout an individual's daily activities, currently (as of this application's filing date) an unusual possibility, then wireless transmission of all raw data would require an apparatus transmitter duty cycle of 2% or less, which may be acceptable in view of available device battery power and the cost of wireless access. On the other hand, wireless access currently available supports data transmission rates at best of 14.4 kbits/sec. At these rates the apparatus transmitter would have a virtually 100% duty cycle, which is likely to be an unacceptable power and wireless access cost.

Alternatively, data may be stored locally in microprocessor unit 3 and transmitted periodically only in bulk. For example, a commonly available 64 MB flash memory module may easily store raw data for 12 or more hours. A 128 MB module could hold 24 hours of data. A full flash memory module may be replaced and sent by overnight mail services to the central repository. Alternatively, the data may be sent by high-speed wired digital connection (e.g., DSL or cable modem to internet) directly to the central repository. Other removable memory technologies, for example, micro-hard-drives or micro ZIP drives, may also be used. In this embodiment, unit 3 may communicate wirelessly only important or significant physiological events, such as alarms recognized. This would be a much smaller amount of data easily transmitted currently in most locations.

Therefore, depending on available wireless data rates and access cost, on available apparatus battery power, and available removable memory capacities, the present invention includes microprocessor unit designs from wireless transmission of all raw data to a central repository to local storage of all raw data with periodic transmission. The latter embodiment is currently preferred for most locations.

A further data storage embodiment includes local, private wireless transmission of data from a microprocessor unit of a monitoring garment to a local receiver within a short distance, perhaps 10 to 1000 feet, of the individual being monitored. From the local receiver, the data may be stored at a local computer system, for example a PC-type computer, for periodic transmission to a central repository for access by health care providers. The periodic transmission may be via removable media a few times daily, as described above, or may be via standard or high speed access (DSL or cable modem) perhaps hourly. Alternatively, the central repository may be replaced by a local server PC-type computer accessed by health care providers. Although not changing transmitter duty cycles, local wireless transmission would eliminate access costs to public wireless facilities and may be of higher speed, and therefore, make wireless transmission of raw data a more attractive tradeoff. The embodiment would be appropriate for an individual ambulatory yet confined to a residence, or health care facility, or relatively small workplace. It may not be appropriate for individuals engaging in their normal daily activities.

In an alternative embodiment, the microprocessor may compress the signal data prior to storage. This compression may be implemented in software encoding an appropriate known compression technique. An exemplary technique is to subtract a base carrier frequency from each frequence datum so that recorded frequency data are offset to have a substantially zero average frequency. Further, each offset frequency datum may be recorded as a difference with respect to one or more previous offset frequency data. Periodically, the current carrier frequency and a offset frequency datum may be recorded to synchronize decompression software.

Next, microprocessor unit 3 may optionally recognize alarm conditions and generation alarm signals, which are in all cases audible but may also involve screen-display of visual information. Alarm conditions recognizable by a microprocessor unit of average capabilities are of two basic types. The first type is a discrete temporal event. For example, heart rate increases suddenly to dangerous levels, or paradoxical wall motion is observed, or breathing slows or ceases dangerously. The second type of alarm condition is a trend progressing over one to a few hours. For example, in a congestive heart failure patient, over two hours an increasing respiratory rate, perhaps coupled with sustained cardiac rate changes, may signal early the onset of pulmonary edema. Similar changes may be alarmed for individuals at high altitude to warn early of dangerous forms of mountain sickness. Other discrete and trends that are known to those of skill in the art may also be alarmed. Alternatively, more powerful microprocessor units may recognize more complex alarm conditions, perhaps by employing artificial techniques such as neural networks or rule-based systems.

Finally, power management is an important optional function which may be performed in the microprocessor unit. Preferably, the various electronic modules and sensors that are included in a monitoring apparatus according to the present invention include power management facilities that provide reduced power consumption whenever a module or sensor is not in active use. For example, reduced power consumption may be commanded by control signals generated by the microprocessor unit. Additionally, battery power may be physically a part of unit 3. Alternatively, a separate battery unit could be arranged, for example, in a pocket of garment 1.

5.2.3. Further Monitoring Garment Embodiments

Figure 2:
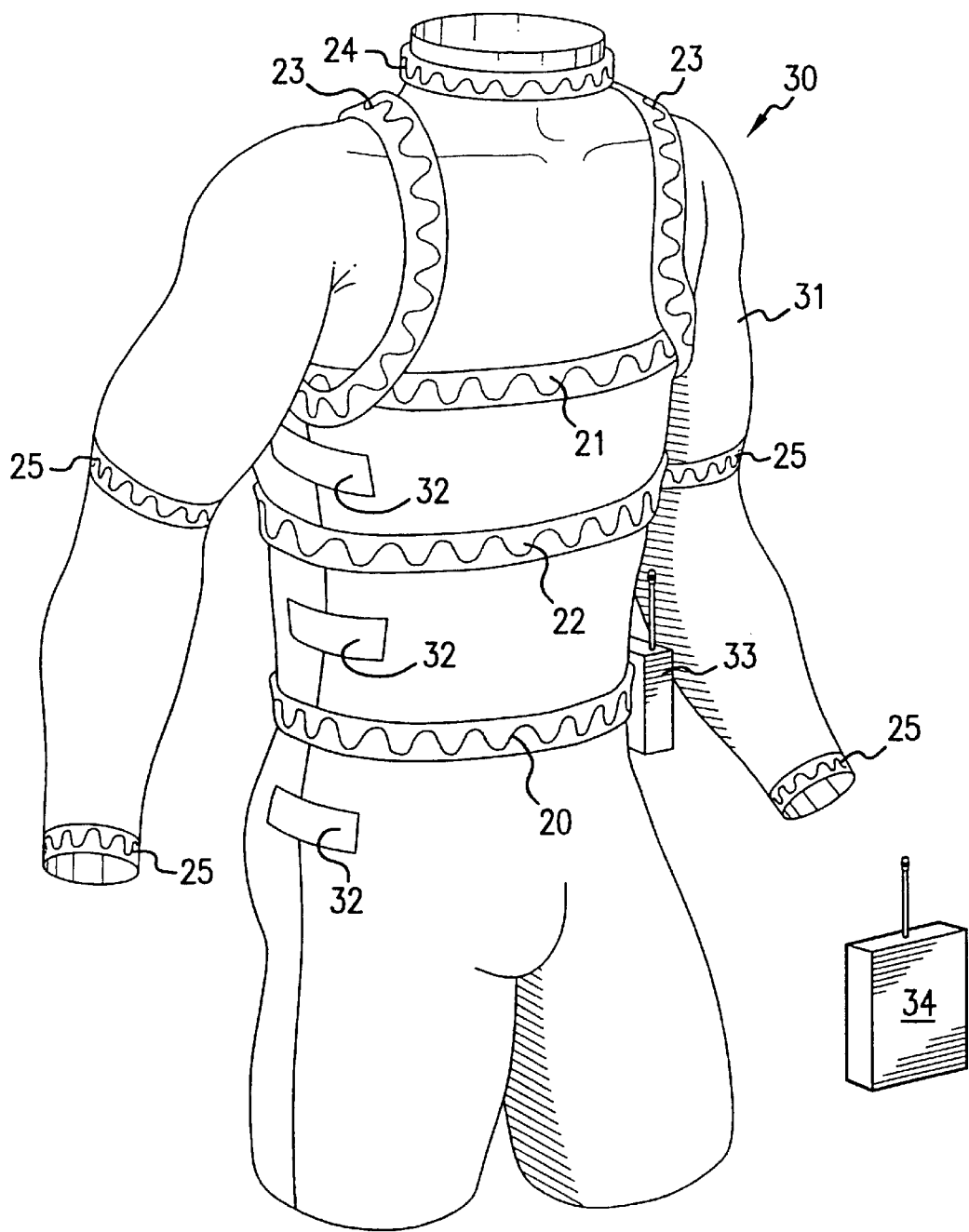
FIG. 2 illustrates a front view of another exemplary monitoring garment constructed in accordance with to the present invention.
Figure 3:
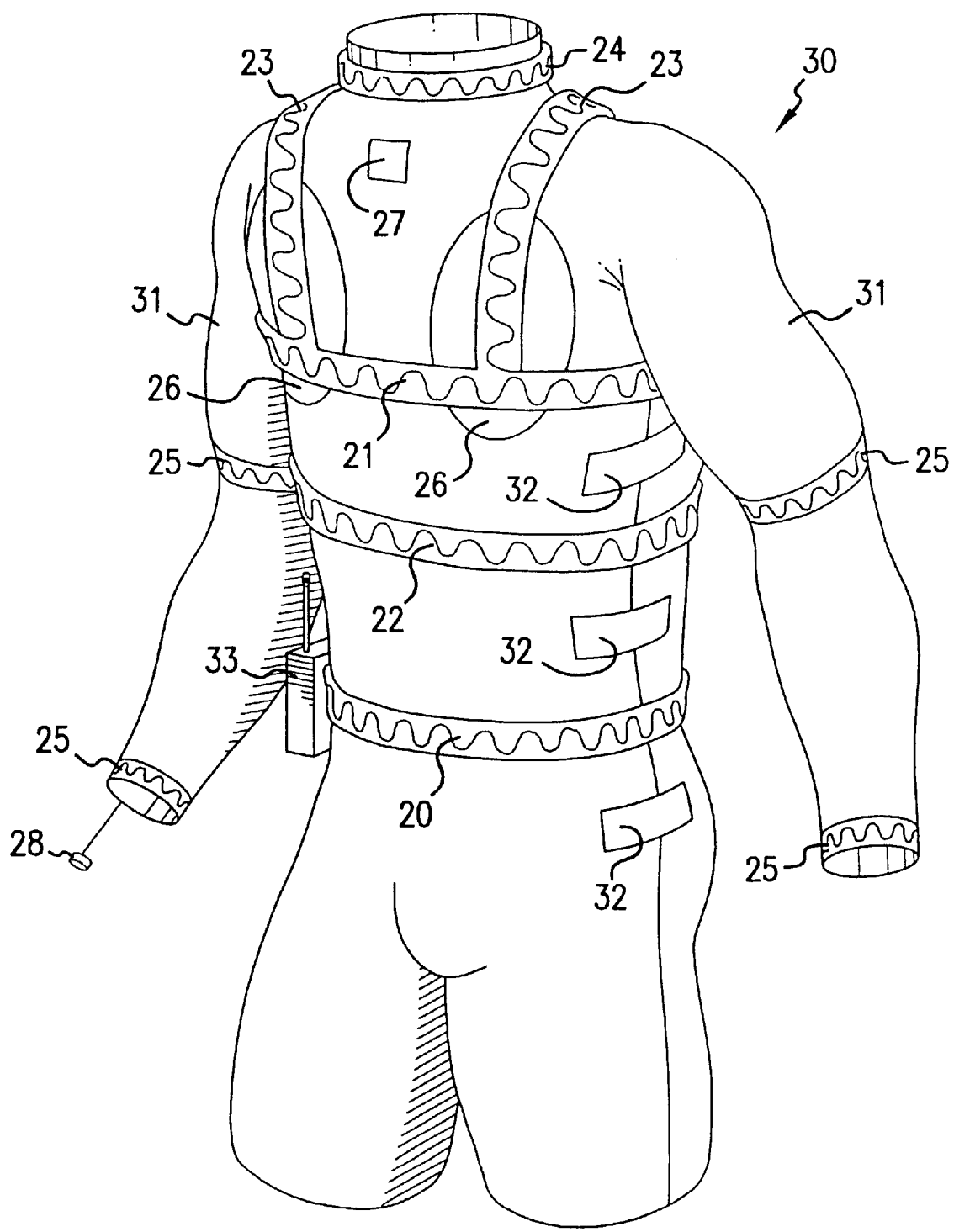
FIG. 3 illustrates a rear view, partly in section, of the monitoring garment of FIG. 2.
Figure 4:
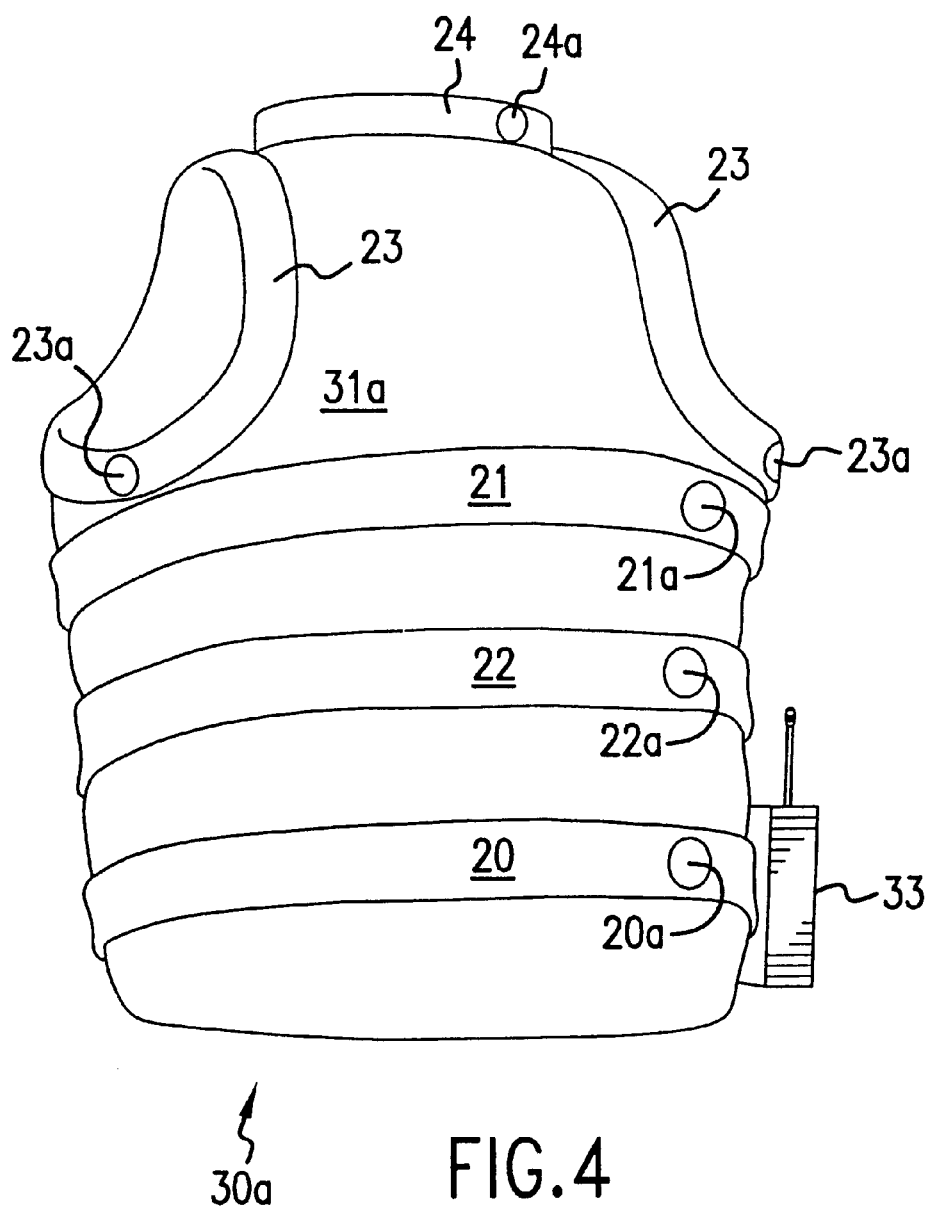
FIG. 4 illustrates a front view of a further exemplary embodiment of a monitoring garment.

Referring now to FIGS. 2 and 3, further embodiments of the non-invasive physiologic monitoring garment 30 comprise inductive plethysmographic sensors 20–25 which are embroidered, sewn, embedded, woven, printed onto or otherwise affixed to or carried on a garment 31 that is worn over and about the torso of an individual to be monitored. As shown in FIGS. 2 and 3, the garment may comprise a turtle-neck long-sleeved garment 31 including portions covering the pelvic region and upper thighs. Instead of the long-sleeved garment 31, the garment in a further embodiment may comprise sleeveless shirt 31a shown in FIG. 4, which does not include the sensors 25. Furthermore, the garment may also be made without the leg portions shown in FIG. 2. Monitoring garment 30 further includes electrocardiographic electrode sensors 26 that may be sewn, embedded, or fixed with adhesive or the like to the inside of the rear face of the garment 31. Alternatively, the electrocardiographic electrode sensors 26 may be directly affixed to the individual to be monitored. The garment 31 may be fastened snugly onto the body using fastening devices 32 such, for example, as velcro strips or ties 16 (see FIGS. 2 and 3). Alternatively, the garment may comprise a shirt without fastening devices as in FIG. 4. In this embodiment, the sensors 20–25 may include an elastic material portion for holding them in place on the individual's torso.

Microprocessor unit 33 comprises, in one embodiment, an oscillator-demodulator (see below) unit for the inductive plethysmographic sensors 20–25, and either has multiplex capabilities or takes the form of a similarity of separate oscillator modules tuned to respectively different frequencies for eliminating cross-talk between the various sensors 20–25. Oscillator modules 20a–24a may also be attached directly to respective inductive plethysmographic sensors 20–24 (see FIG. 4). Alternatively, the oscillator modules may be located directly in the microprocessor unit 33. The microprocessor unit is shown attached to a side of the garment at the waist of the individual to be monitored; it may, however, alternately be attached or carried in any comfortable position or location on or about the body of the individual. As described above, microprocessor unit 33 comprises a recording/alarm unit which collects the monitored signals from the sensors 20–26. Furthermore, microprocessor unit 33 includes a processor for, inter alia, determining alarm conditions and providing data logging functions. Microprocessor unit 33 may also include an output device 45 such, for example, as a sound system optionally with a visual display, for providing alarms and action recommendations to the individual and/or healthcare provider in a preferably area. In an embodiment, the sound system provides these alarms and action recommendations as plainspoken audible statements.

In addition to a sound system that reproduces audible messages, the output device 45 may be a display unit such as a monitor screen that displays the messages. This alternative may for example be used when the individual to be monitored is deaf or hard of hearing, or where the message contains a great deal of information which may be difficult to comprehend or appreciate when merely listening to an audible message. Such a modification also requires an additional signal to be directed to the individual being monitored when a new message is present, since the individual may not be within a line of sight of the monitor screen of the microprocessor unit 33. For this purpose, microprocessor unit 33 may include or activate a signaling device such as a illuminitable lamp for informing the individual being monitored that there is a new message. Since microprocessor unit 33 is mounted on the monitoring garment 30, the signaling device may also when activated effect a vibration of the microprocessor unit 33 which will be felt by the individual being monitored.

Microprocessor unit 33 may be built to include a Personal Digital Assistant (PDA) such as a HandSpring or Palm Pilot or any mobile device capable of wireless communication. In a preferred embodiment, electrodes 20–26 are wired to an electronic module which may be plugged into the microprocessor unit 33. The module uses the processor of the microprocessor unit to perform monitoring, alarming and data logging functions. Furthermore, the monitored signals may be compared to default values to ensure that they are within an acceptable range. If the monitored signal exceeds or falls below the acceptable range of values, the alarm function alerts the individual.

The microprocessor unit may further include input capabilities so that the individual can input information such as symptoms, activities, medications that have been taken, and mood. These input capabilities may be menu driven such that the individual merely selects from a list. Alternatively, the individual may input his symptoms by typing on a keyboard or writing on a touch sensitive screen.

The microprocessor unit 33 may also be connected or linked to a receiving unit 34 located at a separate or remote site that is attended by health care providers for transmitting the data received from the monitoring garment 30, and associated alarms and/or messages, to receiving unit 34 so that the health care providers at the remote site may view and analyze the data. Furthermore, the individual may then use the input capabilities to inform the health care professional regarding the symptoms, activities, medications, and mood. The transmission to the remote site may be made via a modem, Internet connection, satellite hookup, cable, or any other communication system or arrangement, such a standard wireless telephone networks. The connection between microprocessor unit 33 and receiving unit 34 may also allow health care providers at the remote site to return information to the microprocessor 33. For example, the health care providers may wish to provide specific instructions to the individual being monitored. In addition, the PDA may log the data received from the monitoring garment 30 to a local or remote database for tracking the condition of the individual and for comparison to other individuals. This enables continued modification and refinement of the diagnostic algorithm in the module or the microprocessor unit 33 and transmission of action recommendations from the receiving unit 34 to the microprocessor unit.

The monitoring garment 30 or 30a may transmit data to the receiving unit at a rate ranging from approximately 1–1000 points/second (depending on the available sensors). Optionally, a one minute trend numerical value reduced from data processed waveforms is transmitted every five to ten minutes in which case the monitoring garment may transmit data at the rate ranging from approximately 1–1000 points/second only when an adverse or preprogrammed event occurs to thereby conserve the batteries powering the microprocessor unit 33 on the monitoring garment.

The structure and operative functionality of the individual sensors 20–26 will now be explained in further detail. A neck inductive plethysmographic sensor 24 is sewn, embroidered, or embedded, for example, to the area of garment 31 or 31a. Sensor 24 monitors jugular venous pulse, carotid arterial pulse, intrapleural pressure swings related to respiration, contraction of neck muscles, and swallowing deflections. Estimations of the central venous pressure from the data collected by sensor 24 compares well to values simultaneous recorded using intravascular catheters. Since the jugular venous pulse depicts an 'a' wave related to atrial contraction, which is a substitute for the 'P' wave of the electrocardiogram, data from sensor 24 may aid in differentiating arrythmias and supraventricular tachycardia with aberrant ventricular conduction from ventricular tachycardia. The recording of the arterial pulse in conjunction with an electrocardiograph allows computation of the systolic time intervals which may be used for estimating the mechanical function of the left ventricle. Sensor 24 may also record swallowing deflections as sharp, transient waveforms superimposed upon slower respiratory deflections and vascular pulses.

An abdominal plethysmographic sensor 20 and a rib cage plethysmographic sensor 21 are sewn, embroidered, or embedded, for example, in the abdominal and rib cage portions of garment 31 or 31a for monitoring the expansion and contraction of the abdomen and rib cage, respectively. Sensors 20 and 21, used together, are referred to as a respiratory inductive plethysmograph and are employed for recording breathing patterns.

A thoracic inductive plethysmograph sensor 22 is sewn, embroidered, or embedded, for example, into garment 31 or 31a around the xiphoid process region. Sensor 22 may be formed of one or more plethysmographic coil-type sensors and operatively monitors the beat by beat ventricular volume during breath holding and during slow breathing. Analysis of the resulting waveforms by the microprocessor unit recording/alarm unit 40 enables computation of changes in cardiac output and stroke volume and of parameters related to systolic and diastolic functions. Analysis of a derivative of the ventricular waveforms yields parameters analogous to Echo-Doppler measurements of the mitral valve. The deceleration time of the mitral flow velocity parameter can provide an estimate of pulmonary capillary wedge pressure in individuals with compromised left ventricular function. Longer deceleration times are consistent with normal and shorter times with elevated pulmonary capillary wedge pressures.

Two hemithoracic inductive plethysmographic sensors 23 are sewn, embroidered, or embedded, for example, into garment 31 or 31a on the right and left sides of the upper thorax. These sensors 23 enable measurement of inequalities in regional expansion with breathing and paradoxical motion between the two hemithoraces. Such inequalities suggest pleural effusion, diaphragmatic hemiparesis, or pneumothorax and may aid in diagnosis of certain clinical circumstances.

Limb inductive plethysmographic sensors 25 are sewn, embroidered, or embedded, for example, at the elbow and wrist areas of the garment 31. Sensors 25 record vascular pulses over the vessels of the limb or extremity about which it is placed. Sensors 25 may be used to record peripheral blood flow using standard plethysmographic occlusion techniques, pulse transit time by using a pair of separated sensors 25 on the extremity, or pulse transit time from arterial pulse in the neck to the extremity. Sensors 25 may also provide wide-band external pulse recording of systematic blood pressure during cuff deflation.

The preferred embodiment of monitoring garment 30 further includes electrocardiogram (ECG) electrode sensors 26 (FIG. 3). As stated above, the ECG electrode sensor may be mounted on the monitoring garment 30 or, alternatively, may be directly applied to the individuals body and connected to the PDA 33 via a wire.

The combination of RR intervals of the ECG measurements from sensors 26 and the tidal breath waveform from the respiratory inductive plethysmographic sensors 20 and 21 as described above may be used to determine respiratory sinus arrhythmia which is a measure of autonomic nervous system function. High values of this measure signify predominant parasympathetic nervous system activity and low values predominant sympathetic nervous system activity.

A body position sensor 27 may also be sewn, embroidered, or embedded, for example, in garment 31 or 31a to indicate the individual's posture. Body position sensor 27 may comprise one or more standard available accelerometers.

Finally, pulse oximeter sensor 28 (FIG. 3) may also be used in conjunction with the monitoring garment 30 or 30a.

Pulse oximeter sensor 28 is generally placed at a distal fingertip of the individual or subject to measure arterial oxygen saturation and body movements. Although pulse oximeter 28 need not be carried on or as a direct component of the monitoring garment 30, detected information from oximeter 28 may be treated in a manner similar to data from sensors 20–26 by microprocessor unit 33. True values of arterial oxygen saturation are thereby distinguishable from values affected by motion artifacts using appropriate software algorithms.

The recording/alarm functions of the microprocessor unit 33 operatively provides, by way of illustrative example, the following functionality:

(1) messages assuring proper functioning of the monitor, such for example, as "system operating properly";

(2) messages concerning actions to be taken in the event of malfunction, such, for example, as "system not operating properly, make sure the disk is inserted properly", or "system malfunction, contact the equipment manufacturer" (the name and address may also be supplied);

(3) messages concerning correct or incorrect placement and detachment of sensors 20–26 and their lead wires;

(4) messages relating to vital signs information, significance, and actions to be taken by the individual in response thereto;

(5) periodic messages concerning the stability of vital signs at preselected intervals or upon request of the individual or health care provider for assurance purposes, such for example, as "it is now 10 AM and there has been no change in the vital signs";

(6) messages relating to specialized physiologic parameters information, significance, and recommended actions in response thereto;

(7) directions including instructions entered by an attending health care provider, and (8) reminders directing the individual to take medications (the recording unit may log compliance by monitoring when the individual swallows if the medication is to be taken orally, or monitoring breathing patterns if the medication is to be taken is in aerosol form).

In addition to providing such messages, the recording/alarm function may monitor the individual for effectiveness and proper functioning of assisted ventilatory and continuous positive air pressure (CPAP) devices. The recording/alarm function also logs data into a database as physiologic waveforms for one-minute numerical trends which may be transmitted to the remote receiving unit 34 automatically or upon receipt of a request for review by the provider at the remote receiving unit 34.

Instead of concurrently collecting data from all of the sensors and detectors of the monitoring garment 30 or 30a the types of physiologic parameters to be monitored may be limited as a function of the specific condition of the individual. Furthermore, garment 31 may comprise any combination of sleeves, turtle neck, and leggings as required by the specific condition of the individual. For example, if an individual has asthma, pertinent parameters such as respiratory drive/ventilation (peak inspiratory flow/ventilation and/or peak inspiratory acceleration/ventilation) should be monitored closely as non-invasive parameters of increasing bronchospasm above a predetermined threshold. This measure will be utilized to provide directions to the monitored individual via output device 45, such for example, as "you have signs of bronchospasm; please take your aerosol medication now!" If aerosol medication is taken correctly and the proper breath holding pattern is observed by the microprocessor unit 33, then output device may state, "aerosol taken, good!" If after 30 minutes, there is no improvement or there is a worsening of specific measures and/or vital signs, the microprocessor unit 33 may state, "call your doctor immediately!" or "get transportation and go immediately to the emergency room."

As another specific example, if the individual has chronic heart failure, then the deceleration time from the derivative of the left ventricular volume curve obtained with the thoracocardiograph, the central venous pressure and respiratory sinus arrhythmia should be closely monitored. The deceleration time has been found to be the most predictive parameter that hospital admission is needed for treatment of chronic heart failure. In one study, values below 125 msec were the threshold associated with required hospital admission. Thresholds may be programmed into microprocessor unit 33 that instructions are delivered to the individual being monitored before the 125 msec level is reached. For example, if the baseline deceleration time of 160 msec falls to 140 msec, then microprocessor unit 33 may state, "take an additional diuretic tablet today at 5 PM." If the deceleration time falls to 120 msec, the microprocessor unit may state, "call your physician immediately." Central venous pressure reflects fluid balance in the body; low values indicate hypovolemia as might take place with overdosing with diuretics, and high values with increasing severity of heart failure. Thus, if CVP on one day is 8 cm $H_2O$ and the following day is 4 cm $H_2O$, the microprocessor unit might state "call your doctor immediately for advice on your medications."

With regard to the monitoring of medicine taking compliance, the desired times of day for taking medications are programmed into microprocessor unit 33. At appropriate times, the unit may state "take one capsule of #1—or one capsule of verapamid now!" Microprocessor unit 33 may also include input devices such as, for example, a bar code reader or other reader so that when the individual takes out a medication vial with a bar code, information from the bar code is passed to the optional bar code reader. Alternately, the individual may enter information on the medications using a manual input device such as, for example, a keyboard or a simple array of buttons as stated above. By clicking or pressing one of the buttons, the individual being monitored manually updates the recording/alarm device to indicate compliance with the scheduled medicine. As mentioned above, when the individual takes medication, swallows may be logged from the neck inductive plethysmograph waveform, thereby suggesting compliance. After the taking of medication, the individual may pass the vial over the optical reader or activate a switch to create window timing marks in the data stream that can be analyzed and stored in microprocessor unit 33 and/or receiving unit 34.

The physiologic parameters may also be programmed for monitoring effectiveness based upon CPAP or BiPAP ventilatory requirements. Nocturnal CPAP and BiPAP are often used for treatment of the obstructive sleep apnea syndrome, which is marked by apneas and increases in upper airway inspiratory resistance. The ratio of peak inspiratory flow to mean inspiratory flow (PIF/MIF), derived from the tidal volume waveform of the respiratory inductive plethysmograph 20 and 21, provides a numerical value for the shape of the inspiratory flow curve. An unobstructed inspiratory flow contour has a sinusoidal shape and the value of this parameter, PIF/MIF, is/2=1.57. As an inspiratory obstruction develops, the inspiratory flow waveform becomes flattened and approaches a PIF/MIF value of 1.0. Significant flattening begins with a threshold value at or below 1.3. In some instances, inspiratory obstruction is marked by a brief prominent spike near beginning inspiration that gives PIF/MIF values of approximately 1.85 or greater. Therefore, optimum CPAP should provide values ranging from 1.3 to 1.85. If PIF/MF is found to be equivalent to 1.2 for a predetermined period of time, then the recording/alarm unit may deliver a message to the individual or to the personal health care provider, with increasing decibels of sound until the problem is corrected, stating "increase CPAP 3 cm water pressure now". Algorithms have been described for automatic adjustment of the level of CPAP pressure based upon indices related to the shape of the inspiratory flow curve.

Since CPAP is generally administered using a nasal mask, it is subject to leaks, particularly at the mask-skin interface. Leaks can be discerned by the recording/alarm unit 34 by comparing the tidal volumes between the values delivered from the CPAP apparatus and those received by the individual. The latter is obtained with respiratory inductive plethysmography using the sensors 20 and 21. For example, if the inspiratory volume per breath from respiratory inductive plethysmography sensors 20 and 21 was found to be 200 ml and the volume delivered by the CPAP device is 500 ml, then a leak in the CPAP system of 300 ml is indicated and the recording/alarm unit may state "wake up and adjust your mask, it is leaking." Mask leaks are also a problem in administering ventilatory support to individuals with respiratory failure or respiratory muscle weakness. Monitoring of volumes delivered versus volumes received is effective in diagnosing such leaks.

5.2.4. Further Electronics Embodiments

Figure 5:
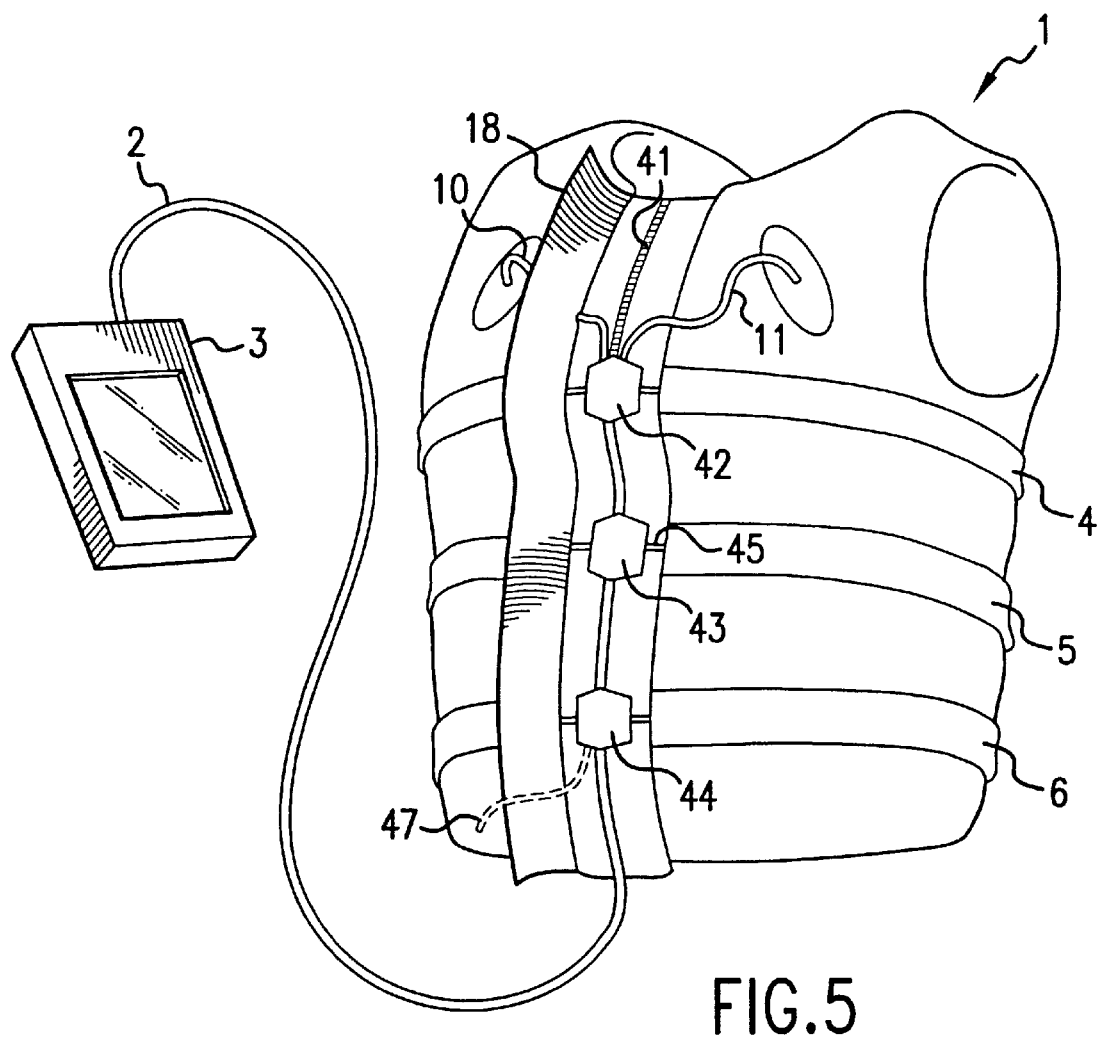
FIG. 5 illustrates a further view of the monitoring apparatus of FIG. 1.

The present invention includes several possible distributions of electronic circuitry between electronic modules carried on garment 1, which are associated with sensors on this garment, and unit 3. FIG. 5 illustrates options for the physical distribution of circuitry, primarily circuitry for processing inductive plethysmographic signals. Here, as before garment 1 includes inductive plethysmographic sensor bands 4, 5, and 6 which are connected to microprocessor unit 3 by primary signal cable 2. Also present at ECG leads 10 and 11 along with a third lead 47 arranged underneath garment 1. Together these leads collect signals representative of a standard 3-lead ECG.

FIG. 5 principally illustrates electronic modules 42, 43, and 44 connected as at 45, to the flexible conductors in the sensor bands, and physically close to the sensors. When the garment is zippered, or otherwise fastened, these modules may support connectors for bridging the conductive loops across the garment division. These modules are disposed underneath flap 18, which is here illustrated as opened, for example when a monitored individual is in the process of "wiring-up" during dressing (or undressing). This flap may be held normally closed by, for example, velcro strips. Also illustrated is fastener 41 (partially hidden by the extension of signal cable 2), such as a zipper, which facilitates dressing by opening the garment. Also facilitating dressing, flexible inductive plethysmographic conductors may plug and unplug into the local modules. Alternatively, for simplicity, the ECG leads may be permanently attached, or they may also plug and unplug from the modules.

The local electronics modules optionally contain circuitry for initial processing of the inductive plethysmographic signals, while circuitry for final processing is carried in unit 3. These modules may also contain initial processing circuitry for other sensors. For example, modules 42 and 43 may contain ECG circuitry, perhaps simply analog pre-amplification and filtering or perhaps also A/D conversion.

Preferably, these electronics modules are permanently attached to the signal cable to minimize the number of parts to be handled during wiring up. Alternatively, these modules may be retained in pockets in the monitoring garment, and plugged and unplugged from the signal cable during wiring up.

Figure 6:
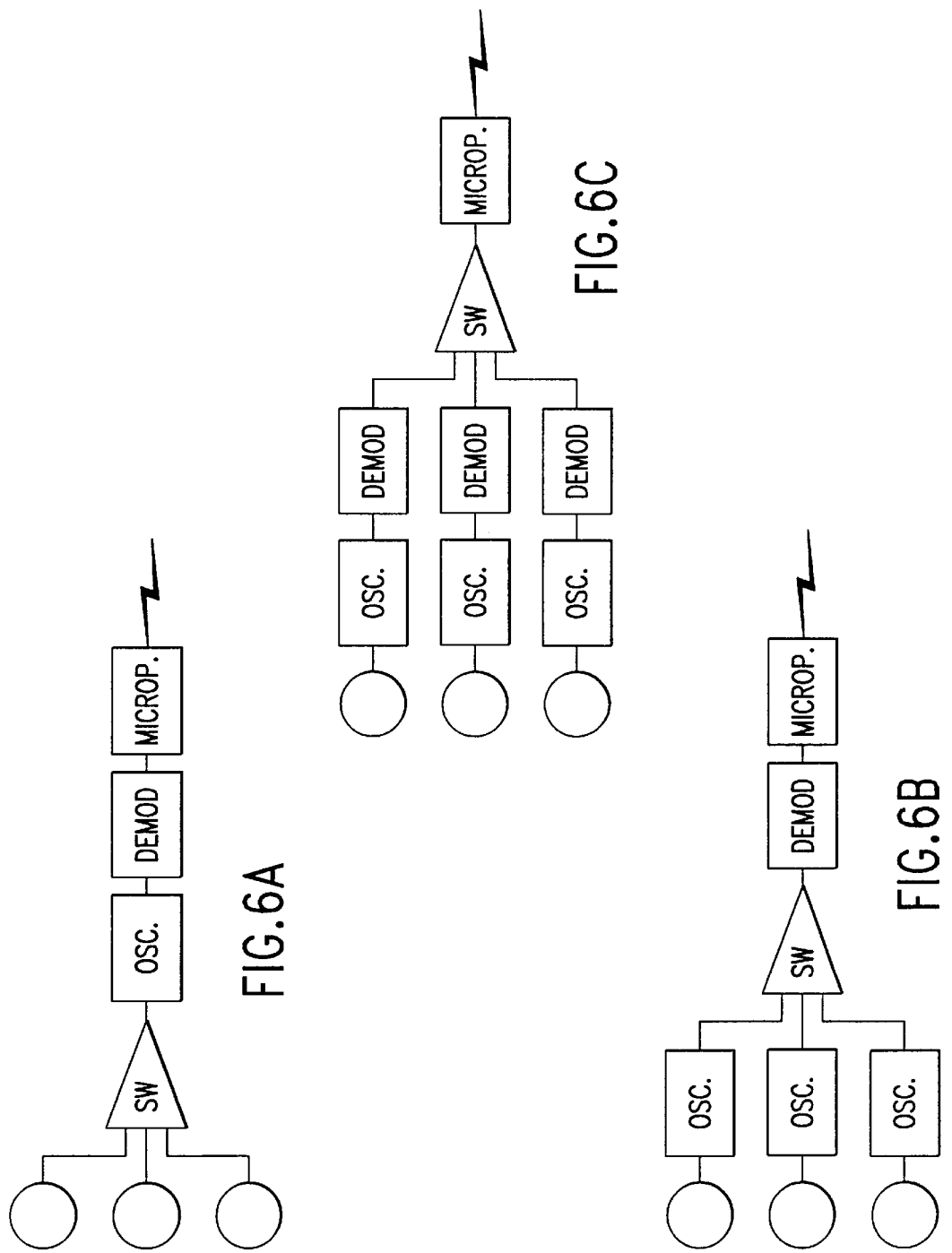

Next, FIGS. 6 and 7 illustrate possible functional distributions of electronic circuitry for processing the plethysmographic signals. With respect to FIGS. 6A–C, the functions of the osc (oscillator) block(s), the demod (demodulator) block(s) and the microp (microprocessor) block are substantially the same and will be described once with respect to FIG. 6A. First illustrated are three conductive loops coupled to a single or to individual oscillators. The oscillators are LC oscillators with a frequency responsive to variations in the loop inductance, and may be of any type known in the art. They preferably are of very low drift due to temperature and other compensations.

Preferably, the loops are coupled to the oscillator(s) through an impedance step-up transformer which steps-up the loop impedance so that reasonable values of capacitor C (for example, greater than 1,000 pf) may be used leading to stable oscillator function. The impedance step-up also multiplies loop-inductance variations leading to a greater signal range. Further, the transformer provides an uninterrupted loop circuit isolated from the powered electronic circuitry. This isolation improves individual safety. Loop isolation is also improved by slightly offsetting the resonant frequency of each loop, for example, by 10 to 50 kHz. Finally, it has been found important that the total loop resistance by low, no more than approximately 1 $\Omega$, to achieve a high Q factor.

The demod blocks demodulate the variable frequency oscillator signal in the sense that they measure the frequency and provide digital data to the microp block. Their function is further described with reference to FIG. 7.

The microp block includes a microprocessor programmed to perform, inter alia, the functions described above including the basic data entry, storage, and communication function. This block may be based on a commercially available PDA-like device, or may be custom designed. In either case, it will be understood to include a microprocessor and supporting components, typically including RAM and ROM memory, a display interface, user input-output interfaces, a communications interface or an interface to removable media, and so forth. The memories will be loaded with programs translated from any convenient programming language.

In view of this general description, FIG. 6A illustrates an embodiment with a single instance of all functional blocks switched between and shared by the three inductive plethysmographic loops. Here, local modules 42, 43, and 44 would include little more than connectors from the conductive loops for bridging any division in the garment and to signal leads to the electronic functional blocks housed in unit 3. As discussed, the entire path between and including the conductive loops and the step-up transformer in the osc block preferably has a resistance of less than 1 $\Omega$. Therefore, the switch SW is preferably a low resistance controllable switch for analog radio-frequency signals. Such a switch is currently available from Dallas Semiconductor/Maxim. Where such a switch is available a low cost, FIG. 6A is a more preferred embodiment. Further, the conductors from the conductive loops to unit 3 should have a substantially small, fixed inductance to avoid adding artifacts to the inductance signals of interest. Preferably, these conductors are from small gauge coaxial cable.

Next, FIG. 6B illustrates an embodiment in which single demod and microp blocks are shared between three inductive plethysmographic loops, each loop having a dedicated oscillator. Preferably, the oscillators have digitized variable frequency output (e.g., a variable frequency square wave), and switch SW may be a standard controllable digital switch. Here, local modules include the osc blocks. FIG. 6B is a preferred embodiment.

Finally, FIG. 6C illustrates a third embodiment in which only the microp block is shared and in which the local modules include both the osc and the demod blocks. This is the currently less preferred embodiment, but may be more advantageous where the osc and demod blocks can be implemented on a single mixed-type integrated circuit (IC).

The operation of the demod block is not described in more detail with reference to FIG. 7, in which portions of the embodiment of FIG. 6B is illustrated in more detail. In general, the demod block is a frequency counter which samples a digitized variable frequency input of from 200 to 400 kHz, and produces a digital frequency output accurate to at least 10 ppm (more preferably to 5 ppm, and even more preferably to 1 ppm). The output is preferably 24 bits or more. While any such frequency counter may be used in the present invention, FIG. 7 illustrates a particular such counter that can be economically implemented as a single programmed logic array IC.

FIG. 7 illustrates only two inductive plethysmographic loops, each with a dedicated osc block, OSC 1 and OSC 2, respectively. The digitized oscillator output is sampled by controllable switch SW and directed to the demod block components. Also input to the demod block is a 96 MHz clock signal. Other, preferably higher clock frequencies may be used, 96 MHz being merely a convenient frequency less that the about 120 MHz which the 80 ns logic in the current implementation is capable. The clock signal is divided to a 2 kHz clock by FREQ DIV block, which is first applied through an oscillator select block (OSC SEL) to control switch SW to sequentially sample the switched osc blocks for 0.5 ms (=½ kHz). The 2 kHz clock provides for a convenient sampling period, other sampling clock rates could be used. The microprocessor (MICRO-PROC) is also interrupted (IRQ lead) at the 2 kHz clock rate to accept the output digital data through a bus buffer and multiplexer (BUS MUX BUFFER), calculate the frequency from the accepted data, and optionally average two or more successive frequence measurements to determine frequencies in sample periods that are multiples of 0.5 ms, such as 2.5 ms. Finally, the 2 kHz clock is applied to counter. accumulator, and latch components (at the latch and reset, R, inputs) of the demod block to reset this circuitry for the next period of frequency measurement.

Generally, the circuit of FIG. 7 operates by counting the number of 96 MHz clock pulses that occur in the number of oscillator periods that occur in a particular 0.5 ms sampling interval (or sampling interval of other length). The components in oval 60 count the oscillator periods in a sampling interval. The OSC CNT block is an 8 bit digital counter that counts the 200–400 kHz oscillator periods in the sampling interval, this count being latched into the OSC CNT LATCH and the counter reset every 0.5 ms. This eight bit count is supplied to the microprocessor through the BUS MUX BUFFER. Next, the components in oval 61 count the number of 96 MHz clock periods that occur in the counted number of oscillator periods. The TIMER CNT block is a 16 bit digital counter that counts clock periods. Since this count is latched into the TIMER CNT ACCUM block only on the occurrence of oscillator pulses applied to this block by lead 62, this accumulator block only contains counts of clock pulses within completed oscillator periods. At the end of a sampling period, the 16 bit count is latched into the TIMER LATCH, the counters are reset, and the 16 bit count is made available to the microprocessor through the BUS MUX BUFFER.

One of skill in the art will appreciate other equivalent circuit arrangements that are capable of obtaining these counts. In particular, not illustrated in FIG. 7 is hold circuitry, which prevents any activity for the first few (2–4) oscillator periods. This permits both accurate starting of the clock count as well as provides for circuit stabilization.

Finally, the MICRO-PROC divides the 8 bit oscillator period count by the 16 bit clock period count to obtain a 24 bit measured oscillator frequency. Note that it is oscillator period (the inverse of frequency) which varies directly with changes in cross sectional area as measured by the inductive loop.

Thus the demod block of FIG. 7 has a random error of one-half of a 96 MHz clock period, or 5.2 ns, during every 0.5 ms sampling interval. This is a less than 10 ppm error that may be reduced by averaging; for example, averaging for 2.5 ms results in a less than approximately 2 ppm error. Thus the demod block of FIG. 7 achieves the accuracy required for inductive plethysmography. On the other hand, if the demod merely counted the number of oscillator cycles within a 0.5 ms sampling interval, then the random error would be one-half of an approximately 300 kHz period, or 1.67 µs every 0.5 ms, of about 3300 ppm. Such inaccuracies would totally hide both respiratory and cardiac inductive plethysmographic signals, which at most have an amplitude to 1000 ppm.

5.3. Systems and Methods

FIG. 10 illustrates overall methods of operation of a system according to the present invention incorporating a monitoring apparatus according to the present invention. Here, monitored individual 80 is illustrated as wearing a monitoring garment and holding (for data entry) a microprocessor unit (collectively, monitoring apparatus) according to preferred embodiments of the present invention.

The microprocessor unit may generate information and alarms directly to the monitored individual. Preferably, all data collected by the monitoring apparatus, including all raw data, is stored at a repository. Central repository 91, which is usually remote from the monitored individual, may store the date from many monitored individuals in server-type computer systems 86 equipped with database facilities. Monitored individuals may transmit data either by means of removable storage media 81a (such as a flash memory module) or by wireless transmission 81b, or by both means for different quantities and types of data.

Alternatively or additionally, data may be stored at local repository 92 after transmission by local wireless transmission 82. Removable media may also be used locally. In this case, the monitored individual's activities are usually restricted so that a substantial fraction of days are spent within a few hundred to a few thousand feet of the local repository. The local repository may be a PC-type computer with adequate storage, preferably hard disks of at least 10 GB capacity. Further the local repository may transmit 83 stored data periodically to central repository 91 (if present).

Users of this system include monitored individual 80, who enters data on, e.g., activities and symptoms into the microprocessor unit, and may receive medical reminders or alarms warning of conditions needing attention. Another type of user may be local health care professionals 85. These users may receive patient information (and transmit patient information and instructions) through local repository system 84. Local professionals may also receive information 93 from central health care professionals 90 by several means, such as telephone, e-mail, pager, and so forth. This information may provide patient status summaries or specific diagnostic and therapeutic guidance to the local professionals System users associated with the central repository include one or more central professionals 90, who advantageously access the system through local computers or terminals 89 in communication with server system 86. The central professionals oversee the medical status of all monitored individuals whose data is stored at that central repository. To assist these professionals the servers systems may be provided with display programs designed to conveniently survey the monitored population, and also with diagnostic or therapeutic programs which provide specific medical guidance perhaps by employing artificial intelligence techniques.

Also, monitoring users 88 are associated with central repository 91, which they access by local computers or terminals 87. These users oversee the technical operations of the monitoring apparatus of the monitored population, the operation of system computers and communications, and processing programs and resolve any problems. Monitoring users may also provide assistance to other system users in response to messages by telephone, e-mail, or other means. Further, monitoring users may perform important quality control functions by overseeing the substantive function of the system of this invention. Quality control may include ensuring that the system correctly monitors physiological parameters, correctly displays and interprets monitored parameters to the various system users, and is in compliance with all regulatory requirements and guidance.

Finally, all system components incorporate security measures sufficient to meet mandated and preferable privacy requirements. These measures may include user authentication and data encryption as is known in the art.

5.4. Additional Embodiments

Many additional embodiments will be apparent to one of skill in the art; come of which are described here.

Additional Inductive Plethysmographic Sensors

Additional plethysmographic sensors may be incorporated in the monitoring apparatus of this invention. First, the data gathered by existing sensors can be augmented with additional sensors. For example, by adding one or more thoracic sensor bands superior to the already described cardiac band positioned at the level of the xiphoid process further information about cardiac function may be obtained.

Further, additional bands may provide new types of information. A sensor of a lower-abdominal cross-sectional area may be used to detect uterine contractions indicating the onset of labor in a pregnant female. Also, such a lower abdominal sensor may detect the present of intestinal gas and flatus.

An inductive plethysmographic sensor of a mid-abdominal cross-section, may monitor general intestinal activity. For example, absence of cross-sectional area variations may indicate a "silent abdomen," which is often a surgical emergency. Such monitoring may be advantageous in patients recovering from abdominal surgery.

Further, particular monitoring tasks may require higher accuracies or rates, or may permit reduced accuracies or rates. Appropriate accuracies and rates may be easily determined by one of skill in the art in view of the monitoring task and the associated circuitry may be modified. For example, higher accuracies may be achieved by a demodulator circuit with higher clock frequencies or longer sampling intervals.

Generally, a garment may be "prescribed" for an individual according to his medical condition. Such a prescribed garment would have more or fewer sensors so that only signals bearing on physiological parameters of interest are obtained and stored.

A Multi-Band Garment

A shirt-like garment may be constructed with a larger number of inductive plethysmographic sensor bands, for example, 10, or 20, or 30, or more bands, which are substantially uniformly distributed long the vertical axis of the torso. Signals from these bands may be multiplexed into a smaller number of local electronic modules, which communicate with a microprocessor unit (or computer system) sufficiently capable to handle the increased data rate.

This larger number of signals may have several uses. First, they may be used for research in developing sensor bands for detecting additional physiologic parameters, or for detecting current parameters with increased reliability for individual difficult to monitor because of activity or body habitus. Second, the can be used in selecting a cut and arrangement of a monitoring garment for particular individuals. An individual may wear a multi-band garment for a short time, and the associated processing unit may determine which bands are best at detecting desired physiological parameters. A final garment may then be tailored with a cut, fit, and sensor band location best suited for that individual. This may replace garments fit to be adequate for a range of individuals, though ideal perhaps few or none. Third, a multi-band garment may be worn for regular monitoring, the few actual bands from which data is stored and communicated being selected in real time by the associated microprocessor unit as those with the best signals.

Wireless Transmission Within a Single Monitoring Apparatus

With the advance of radio frequency (RF) circuitry and protocols, it may be advantageous to replace at least the primary signal cable by wireless transmission between the inductive plethysmographic sensors and the microprocessor unit. Optionally, all data cables may be eliminated. This is advantageous to simplify use of the monitoring apparatus, with the monitoring garment, for a monitored individual.

FIGS. 8A–B illustrate two principal (and exemplary) embodiments for such local wireless transmission. In these figures, the osc, demod, and microp blocks have the similar meanings to these blocks in FIGS. 6A–C. The xmtr block is a RF transmitter; the rcvr block is an RF receiver; and arrows 70 represent wireless transmission between the xmtr and the rcvr between the monitoring garment and its microprocessor unit. Preferably, the transmissions are of very low power in an un-licensed band, for example, the bands near 900 MHz or 2.4 Ghz. For actual implementation, it is preferable that the xmtr and rcvr locks be implemented at least of single ICs, if not in a higher form of integration embedded in other ICs.

In the embodiment of FIG. 8A, the digitized, 200–400 kHz output of the oscillators is transmitted from the modules associated with the plethysmographic sensors to the microprocessor unit. In order that variations in frequency by adequately demodulated, it is advantageous for a carrier-type timing signal be transmitted so that the xmtr and rcvr may be in phase lock. Circuitry similar to that used in portable phones may be employed.

In the embodiment of FIG. 8B, 8 and 16 bit digital words are transmitted from the sensors. Such digital transmission is advantageously by means of evolving standards and products for local digital transmission, such as the standard being developed by the Bluetooth consortium. In this embodiment, it may be advantageous to divide the microprocessor functions between a simple microprocessor, microp1, associated with each sensor, and a "central" microprocessor, microp2, in the microprocessor unit. Microp1 may losslessly compress the digital data to reduce wireless data rates and power requirement; microp2 then decompresses the received data. Compression may be as simple as subtraction of the oscillator 200–400 kHz base frequency along with the transmission of runs of successive differences. Other compression techniques may be used.

Multiplexing of the RF transmission may be by frequency division, time division, or other multiplexing means known in the art.

Other division of the electronic function may be combined with local wireless transmission.

In summary, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A monitoring apparatus for non-invasively monitoring physiological parameters of an individual comprising:
   a monitoring garment comprising a shirt for the torso of the individual to be monitored,
   one or more inductive plethysmographic (IP) sensors, each IP sensor comprising an inductance sensor including at least one conductive loop arranged to closely encircle the torso, wherein the inductance of the conductive loop is responsive to the cross-sectional area of the torso enclosed by the loop,
   a cardiac cycle sensor for generating signals responsive to occurrence of cardiac ventricular contractions,
   a signal cable for carrying signals from said sensors, and
   a microprocessor unit comprising a microprocessor for receiving signals from said signal cable and for recording digital data derived from all received signals in a removable computer-readable memory media.

2. The apparatus of claim 1 wherein said cardiac cycle sensor comprises at least one electrocardiogram (ECG) electrode attached to said individual to be monitored.

3. The apparatus of claim 1 wherein said cardiac cycle sensor comprises at least one IP sensor closely fitting about the neck of said individual to be monitored, wherein signals the inductance of the IP sensor is responsive to cardiac ventricular contractions because the cross-sectional area of the neck is responsive to carotid artery pulsations generated by cardiac ventricular contractions and the inductance of the IP sensor is responsive to the cross-sectional area of the neck.

4. The apparatus of claim 1 wherein the computer-readable medium comprises a magnetic disk.

5. The apparatus of claim 1 wherein the computer-readable medium comprises a flash memory module.

6. The apparatus of claim 5 wherein the flash memory module has a capacity of 64 MB or more.

7. The apparatus of claim 1
   wherein said monitoring garment further comprises a band for the neck of the individual to be monitored,
   wherein said IP sensors comprise a neck inductive plethysmographic sensor operatively arranged for generating signals responsive to jugular venous pulse, carotid arterial pulse, respiration-related intra-pleural pressure changes, contraction of neck muscles, and swallowing deflections, and
   wherein the signal cable further comprises an attachment to the conductive loop of the neck IP sensor.

8. The apparatus of claim 1 wherein said IP sensors comprise at least one abdominal IP sensor including one or more conductive loops and at least one rib cage IP sensor including one or more conductive loops operatively arranged for measuring breathing patterns of the patient.

9. The apparatus of claim 1 wherein said IP sensors comprise at least one thoracic IP sensor including one or more conductive loops operatively arranged for measuring ventricular stroke volume.

10. The apparatus of claim 1 wherein said IP sensors comprise at least one lower abdominal IP sensor operatively arranged for measuring intra-lower-abdominal contractions and dilations.

11. The apparatus of claim 1 wherein said IP sensors comprise one or two hemithoracic IP sensors operatively arranged for measuring breathing and paradoxical motion between two hemithoraces of the patient.

12. The apparatus of claim 1 further comprising one or more further sensors attached to the signal cable and selected from a group comprising a body position sensor for indicating a posture of the individual, a pulse oximeter for indicating arterial oxygenation saturation, and a throat microphone for indicating talking and snoring.

13. The apparatus of claim 12 further comprising at least two body position sensors, a first body position sensor mounted on said garment and a second body position sensor mounted elsewhere on the individual.

14. The apparatus of claim 1 wherein said IP inductive plethysmographic sensors are attached to said garment as an integral part of said garment via an attachment consisting of one of sewing, embroidering, embedding, weaving and printing said inductive plethysmographic sensor into said garment.

15. The apparatus of claim 1 wherein said microprocessor unit further comprises an audio device for generating audio indications to the individual being monitored.

16. The apparatus of claim 1 wherein said microprocessor unit further comprises a display unit for displaying viewable messages to the individual being monitored.

17. The apparatus of claim 1 wherein said microprocessor unit further comprises an input unit for the individual being monitored to input information or commands to said microprocessor unit.

18. The apparatus of claim 1 wherein said microprocessor unit further comprises a memory accessible to the microprocessor, and wherein the memory comprises encoded software instructions for causing the microprocessor to read input data and to write output data derived from the input data in the removable computer-readable memory media.

19. The apparatus of claim 18 wherein the memory further comprises encoded software instructions for causing the microprocessor to determine significant physiological events in the individual being monitored and to indicate audibly determined significant events to the individual.

20. The apparatus of claim 19 wherein the microprocessor unit comprises components for wirelessly transmitting determined events.

21. The apparatus of claim 18 wherein the memory further comprises encoded software instructions for causing the microprocessor to determine significant temporal physiological trends in the individual being monitored and to indicate audibly determined significant trends to the individual.

22. The apparatus of claim 21 wherein the microprocessor unit comprises components for wirelessly transmitting determined significant trends.

23. The apparatus of claim 18 wherein the memory further comprises encoded software instructions for causing the microprocessor to compress data before writing to the removable computer-readable memory media.

24. The apparatus of claim 1 wherein the microprocessor unit further comprises circuitry for deriving digital data from non-digital data received from the signal cable.

25. The apparatus of claim 1 wherein said monitoring apparatus further comprises circuitry for generating a variable-frequency signal from each IP sensor, the generated frequency being responsive to the inductance of the conductive loop of the IP sensor, and wherein the microprocessor unit further comprises circuitry for deriving digital data from the generated variable-frequency signals, the digital data comprising encoding of the variable frequency of the signals with errors of 100 ppm or less.

26. A monitoring apparatus for non-invasively monitoring physiological parameters of an individual comprising:
 a monitoring garment comprising a shirt for the torso of the individual to be monitored,
 one or more inductive plethysmographic (IP) sensors, each IP sensor comprising
  (i) a longitudinal band of elastic material attached to said garment for closely encircling the torso,
  (ii) an inductance sensor including at least one flexible conductive loop attached to the longitudinal band, wherein the inductance of the conductive loop is responsive to the cross-sectional area of the torso enclosed by the loop, and
  (iii) a tightening device for adjusting circumferential tightness of the IP sensor to substantially prevent longitudinal movement of the IP sensor along the torso, and
 a microprocessor unit comprising a microprocessor for receiving signals from said IP sensors and for recording digital data derived from all received signals in a removable computer-readable memory media.

27. The apparatus of claim 26 wherein longitudinal motion of each IP sensor is substantially prevented when the physiological parameters indicated by the inductance of the conductive loop of the sensor do not measurably change.

28. The apparatus of claim 26 wherein the monitoring garment comprises excess fabric arranged to permit longitudinal stretching of the torso without applying force to the IP sensors sufficient to cause substantial longitudinal motion.

29. The apparatus of claim 28 wherein longitudinal motion of each IP sensor is substantial if physiological parameters indicated by the inductance of the conductive loop of the sensor change as the monitoring garment is worn by the individual.

30. The apparatus of claim 26 wherein the monitoring garment comprises fabric with sufficient longitudinal elasticity to permit longitudinal stretching of the torso without applying force to the IP sensors sufficient to cause substantial longitudinal motion.

31. The apparatus of claim 26 wherein the tightening device comprises a cinch band and a gripping device for releasably gripping excess cinch band under tension.

32. The apparatus of claim 26 wherein the tightening device comprises a drawstring.

33. The apparatus of claim 26 further comprising a cardiac timing sensor for generating signals responsive to cardiac ventricular contractions, and wherein said microprocessor unit further records digital data derived from signals received from said cardiac timing sensor.

34. The apparatus of claim 26 further comprising a signal cable for carrying signals from said sensors to said microprocessor unit.

35. A monitoring apparatus for non-invasively monitoring physiological parameters of an individual comprising:
 a monitoring garment comprising a shirt for the torso of the individual to be monitored and a longitudinal fastener for opening and closing the shirt,
 one or more inductive plethysmographic (IP) sensors, each IP sensor comprising an inductance sensor including at least one flexible conductive loop arranged to closely encircle the torso, wherein the inductance of the conductive loop is responsive to the cross-sectional area of the torso enclosed by the loop,
 a cardiac timing sensor for generating signals responsive to occurrence of cardiac ventricular contractions,
 a signal cable for carrying signals from said sensors comprising at least one module, wherein the module is coupled to and electrically completes the conductive loops of the IP sensors, wherein termini of the conductive loops may be uncoupled from module, and wherein the module comprises circuitry for generating signals responsive to the IP sensors, and
 a microprocessor unit comprising a microprocessor for receiving signals from said signal cable and for recording digital data derived from all received signals in a removable computer-readable memory media.

36. The apparatus of claim 35 wherein at least one IP sensor further comprises a tightening device for adjusting circumferential tightness of the IP sensor to substantially prevent longitudinal movement of the IP sensor along the torso, and wherein the tightening device can be arranged not to impede unfastening of the shirt.

37. The apparatus of claim 35 wherein the conductive loops of the IP sensors and the module further comprise mating connectors so that the conductive loops may be connected and disconnected from the module.

38. The apparatus of claim 35 wherein the signals generated by the module in response to each IP sensor comprise digital data encoding the frequency of an oscillator responsive to the inductance of the conductive loop of the IP sensor, the frequency being encoded with errors of 100 ppm or less.

39. The apparatus of claim 38 wherein errors of frequency encoding are 10 ppm or less.

40. The apparatus of claim 35 wherein the signals generated by the module in response to each IP sensor comprise signals of variable frequency, the frequency being responsive to the inductance of the conductive loop of the IP sensor.

41. The apparatus of claim 40 wherein the microprocessor unit further comprises circuitry for deriving digital data from the variable-frequency signals generated from each IP sensor, the digital data comprising encoding of the variable frequency of the signals with errors of 100 ppm or less.

42. The apparatus of claim 41 wherein the microprocessor unit further comprises multiplex circuitry for permitting single deriving circuitry to derive digital data from a plurality of variable-frequency signals.

43. A monitoring apparatus for non-invasively monitoring physiological parameters of an individual comprising:
a monitoring garment comprising a shirt for the torso of the individual to be monitored,
one or more inductive plethysmographic (IP) sensors, each IP sensor comprising an inductance sensor including at least one flexible conductive loop arranged to closely encircle the torso, wherein the inductance of the conductive loop is responsive to the cross-sectional area of the torso enclosed by the loop,
a cardiac timing sensor for generating signals responsive to occurrence of cardiac ventricular contractions,
a signal cable for carrying signals directly from the conductive loops of said IP sensors and for carrying signals from said sensor,
electronic circuitry comprising (i) a multiplexing switch for connecting the conductive loop of any one of the IP sensors to an oscillator, the oscillator having an oscillation frequency responsive to the inductance of the conductive loop connected by the multiplexing switch, and (ii) a demodulator operatively coupled to the oscillator and outputting digital data responsive to the oscillation frequency, and
a microprocessor unit comprising a microprocessor for receiving signals from said signal cable and for receiving digital data from said electronic circuitry and for recording digital data from received inputs in a removable computer-readable memory media.

44. The apparatus of claim 43 wherein the digital data responsive to the oscillation frequency has errors of 100 ppm or less.

45. The apparatus of claim 43 wherein the digital data responsive to the oscillation frequency has errors of 10 ppm or less.

46. The apparatus of claim 43 wherein said electronic circuitry is housed in said microprocessor unit.

47. The apparatus of claim 43 wherein the resistance of the data signal cables and the multiplexing switch from the conductive loop of any IP sensor to the oscillator is less than 1 Ω.

48. The apparatus of claim 43 wherein the multiplexing switch is controlled so that oscillator is periodically connected to the conductive loop of each IP sensor for the duration of a sampling period.

49. The apparatus of claim 48 wherein the sampling period is 1 msec or less.

50. The apparatus of claim 48 wherein the digital data output by the demodulator comprises digital data encoding a count of a number cycles of the oscillator occurring within a sampling period and digital data encoding a count of a number of periods of a clock occurring within the counted oscillator cycles.

51. The apparatus of claim 50 wherein said microprocessor unit further comprises a memory accessible to the microprocessor, and wherein the memory comprises encoded software instructions for causing the microprocessor to determine the actual oscillator frequency by dividing the count of the number of oscillator cycles by the count of the number of clock periods.

52. The apparatus of claim 51 wherein the memory further comprises software instructions for causing the microprocessor to determine an more accurate frequency by combining the counts of a plurality of sampling periods.

53. A monitoring apparatus for non-invasively monitoring physiological parameters of an individual comprising:
a monitoring garment comprising a shirt for the torso of the individual to be monitored,
a plurality of sensors, said sensors comprising
(i) one or more inductive plethysmographic (IP) sensors, each IP sensor comprising an inductance sensor including at least one flexible conductive loop arranged to closely encircle the torso, wherein the inductance of the conductive loop is responsive to the cross-sectional area of the torso enclosed by the loop,
wherein at least one sensor comprises a transmitter for wirelessly transmitting signals generated by the sensor within the vicinity of said physiological monitoring apparatus,
a microprocessor unit comprising (i) a receiver for receiving signals wirelessly transmitted from said sensors, and (ii) a microprocessor for accepting the received signals and for recording digital data derived from the received signals in a removable computer-readable memory media.

54. The apparatus of claim 53 wherein at least one sensor generates output signals in a digital form, and wherein the transmitter transmits the generated digital signals.

55. The apparatus of claim 54 wherein the transmitter and the receiver conform to the Bluetooth standard.

56. The apparatus of claim 53 wherein at least one sensor generates variable-frequency analog output signals, and wherein the transmitter output is modulated by generated variable-frequency analog signal.

57. The apparatus of claim 53 wherein all sensors comprise a transmitter for wirelessly transmitting signals generated by the sensor within the vicinity of said physiological monitoring apparatus.

58. The apparatus of claim 53 further comprising a signal cable, wherein the output of at least one sensor is carried to said microprocessor unit by a signal cable, and wherein said microprocessor records digital data derived from signals carried by said signal cable.

59. The apparatus of claim 53 wherein said sensors further comprise a cardiac timing sensor for generating signals responsive to occurrence of cardiac ventricular contractions.

60. A system for the non-invasive physiological monitoring of physiological parameters of at least one individual comprising:
at least one physiological monitoring apparatus comprising a monitoring garment worn on the torso of an individual being monitored, wherein the monitoring apparatus stores in a digital form in a removable computer-readable memory media data, wherein the data is by sensors comprising generated from (i) one or more inductive plethysmographic (IP) sensors flexibly attached to the monitoring garment, and (ii) a cardiac timing sensor for generating signals responsive to cardiac ventricular contractions, and a data repository for reading data from the removable computer-readable memory media that has been recorded by said physiological monitoring apparatus and for storing read data in a data archive, said data repository being remotely located from said physiological monitoring apparatus.

61. The system of claim 60 wherein said physiological monitoring apparatus further transmits data wirelessly, and wherein said data repository further receives data wirelessly that has been transmitted by said physiological monitoring apparatus, and then stores the received data.

62. The system of claim 61 wherein said physiological monitoring apparatus further comprises a microprocessor for processing the generated data for determining physiological events and alarms, and wherein the data wirelessly transmitted comprises the determined physiological events and alarms.

63. The system of claim 61 further comprising a local data repository co-located with said physiological monitoring apparatus, wherein the local data repository receives data wirelessly transmitted by said physiological monitoring apparatus and stores received data in a local data archive, and wherein the local data repository comprises display terminals for making stored data available to local health care professionals.

64. The system of claim 60 wherein said data repository further comprises display terminals for making stored data available to health care professionals and to users monitoring the operation of said system.

65. The system of claim 60 further comprising a plurality of physiological monitoring apparatus, each apparatus for monitoring a different individual, and wherein said data repository reads data from removable computer-readable memory media recorded by said plurality of physiological monitoring apparatus.

66. A computer readable medium comprising data recorded in digital form, wherein the recorded digital data comprises data responsive with errors of 100 ppm or less to the frequency of an oscillator connected to at least one conductive loop of at least one inductive plethysmographic sensor.

* * * * *